United States Patent
Hocken et al.

(10) Patent No.: US 11,216,370 B2
(45) Date of Patent: Jan. 4, 2022

(54) METHODS AND DEVICES THAT UTILIZE HARDWARE TO MOVE BLOCKS OF OPERATING PARAMETER DATA FROM MEMORY TO A REGISTER SET

(71) Applicant: MEDTRONIC, INC., Minneapolis, MN (US)

(72) Inventors: Robert W. Hocken, Scottsdale, AZ (US); Wesley A. Santa, Andover, MN (US); Christopher M. Arnett, Dayton, MN (US); Jalpa S. Shah, Cumming, GA (US); Joel E. Sivula, White Bear Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 225 days.

(21) Appl. No.: 16/275,545

(22) Filed: Feb. 14, 2019

(65) Prior Publication Data
US 2019/0258570 A1 Aug. 22, 2019

Related U.S. Application Data

(60) Provisional application No. 62/633,063, filed on Feb. 20, 2018.

(51) Int. Cl.
*G06F 3/06* (2006.01)
*G06F 12/00* (2006.01)
(Continued)

(52) U.S. Cl.
CPC ......... *G06F 12/06* (2013.01); *A61N 1/36128* (2013.01); *A61N 1/025* (2013.01);
(Continued)

(58) Field of Classification Search
CPC .................................................. G06F 12/06
(Continued)

(56) References Cited

U.S. PATENT DOCUMENTS 4,825,406 A * 4/1989 Bean ............... G06F 13/423
710/38
4,940,904 A * 7/1990 Lin .................. H03K 19/09429
327/256

(Continued)

FOREIGN PATENT DOCUMENTS

EP 2712654 A1 4/2014

OTHER PUBLICATIONS

PCT/Application No. PCT/US2016/029626 International Search Report and Written Opinion, dated Jul. 6, 2016.
(Continued)

*Primary Examiner* — Mohamed M Gebril
(74) *Attorney, Agent, or Firm* — Withers & Keys, LLC

(57) ABSTRACT

A hardware based block moving controller of an active device such as an implantable medical device that provides electrical stimulation reads a parameter data from a block of memory and then writes the parameter data to a designated register set of a component that performs an active function. The block of memory may include data that specifies a size of the block of memory to be moved to the register set. Multiple individual block mover components of the controller may move respective blocks, each responsive to a dedicated trigger or to a same trigger. Furthermore, a given block mover or individual block mover component may have multiple selectable triggers. The block moving hardware based controller may have one or more memory devices to access, and the firmware may write to one memory while the block moving hardware based controller may read from another.

3 Claims, 15 Drawing Sheets

(51) Int. Cl.
*G06F 13/00* (2006.01)
*G06F 12/06* (2006.01)
*A61N 1/36* (2006.01)
*G16H 40/63* (2018.01)
*A61N 1/02* (2006.01)

(52) U.S. Cl.
CPC .. *G06F 2212/1008* (2013.01); *G06F 2212/17* (2013.01); *G16H 40/63* (2018.01)

(58) Field of Classification Search
USPC .......................................................... 711/104
See application file for complete search history.

(56) References Cited

U.S. PATENT DOCUMENTS

| | | | |
|---|---|---|---|
| 5,095,902 A | 3/1992 | Ljungstroem | |
| 5,456,692 A | 10/1995 | Smith, Jr. et al. | |
| 5,535,333 A * | 7/1996 | Allen, Jr. | G06F 13/282 370/402 |
| 5,653,737 A | 8/1997 | van Lake | |
| 6,128,528 A | 10/2000 | Ericksen | |
| 6,195,107 B1 | 2/2001 | Iverson | |
| 6,704,601 B1 | 3/2004 | Amely-Velez et al. | |
| 6,959,213 B2 | 10/2005 | Prutchi et al. | |
| 7,062,625 B1 * | 6/2006 | Shrader | G11C 7/1051 711/105 |
| 7,113,517 B2 * | 9/2006 | Rumph | H04L 47/24 370/395.4 |
| 7,313,443 B2 | 12/2007 | Splett | |
| 7,363,440 B1 * | 4/2008 | Neuman | G06F 13/16 710/29 |
| 7,460,912 B2 | 12/2008 | Hoyme | |
| 7,715,912 B2 | 5/2010 | Rezai et al. | |
| 8,082,033 B2 | 12/2011 | Rezai | |
| 8,131,949 B2 * | 3/2012 | Lin | G06F 13/1605 711/151 |
| 8,532,784 B2 | 2/2013 | Sherman | |
| 8,578,118 B2 | 11/2013 | Klechner et al. | |
| 9,038,073 B2 * | 5/2015 | Kohlenz | G06F 9/5044 718/100 |
| 10,339,081 B2 | 7/2019 | Hocken | |
| 2007/0288683 A1 * | 12/2007 | Panabaker | G06F 12/0638 711/101 |
| 2008/0130654 A1 * | 6/2008 | Schmidt | G01R 13/0254 370/395.7 |
| 2008/0140902 A1 * | 6/2008 | Townsend | H03F 1/3241 710/306 |
| 2008/0282041 A1 * | 11/2008 | Hartwich | H04L 49/90 711/147 |
| 2009/0003119 A1 * | 1/2009 | Guo | G06F 13/4239 365/230.05 |
| 2010/0194196 A1 * | 8/2010 | Jouper | H02J 1/14 307/31 |
| 2011/0310691 A1 * | 12/2011 | Zhou | G11C 7/1075 365/230.03 |
| 2012/0158096 A1 * | 6/2012 | Sherman | A61N 1/36071 607/59 |
| 2013/0227235 A1 | 8/2013 | Berenbaum | |
| 2013/0335095 A1 * | 12/2013 | Kiuchi | B60L 58/18 324/426 |
| 2014/0277231 A1 | 2/2014 | Berneman | |
| 2014/0281123 A1 * | 9/2014 | Weber | G06F 12/0868 711/103 |
| 2014/0282559 A1 * | 9/2014 | Verduzco | G06F 9/4856 718/102 |
| 2015/0151131 A1 | 6/2015 | Huelskamp | |
| 2015/0242201 A1 * | 8/2015 | Kim | G06F 8/654 717/168 |
| 2015/0297890 A1 * | 10/2015 | Spahr | A61B 5/125 607/57 |
| 2016/0179675 A1 * | 6/2016 | Fahim | G06F 11/08 711/108 |
| 2016/0378537 A1 * | 12/2016 | Zou | G06F 9/4856 718/1 |
| 2017/0270007 A1 * | 9/2017 | Huang | G06F 11/1448 |
| 2018/0024926 A1 * | 1/2018 | Penney | G06F 12/0215 711/141 |
| 2019/0258570 A1 * | 8/2019 | Hocken | G16H 20/40 |

OTHER PUBLICATIONS

U.S. Appl. No. 16/450,905 Office Action, dated Dec. 31, 2019.
U.S. Appl. No. 15/572,777 Notice of Allowance, dated Feb. 21, 2019.
U.S. Appl. No. 16/450,905, filed Jun. 24, 2019.

* cited by examiner

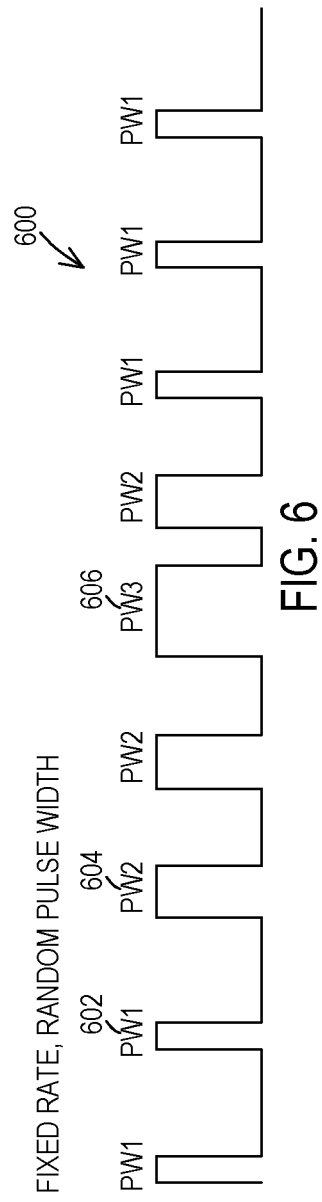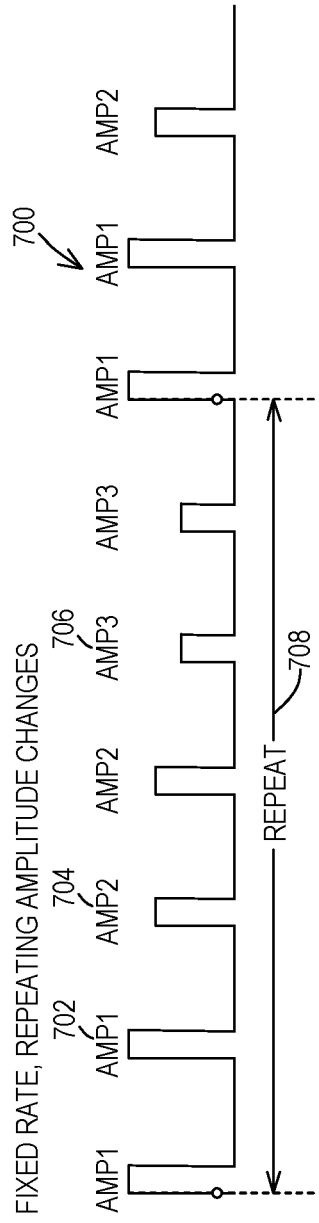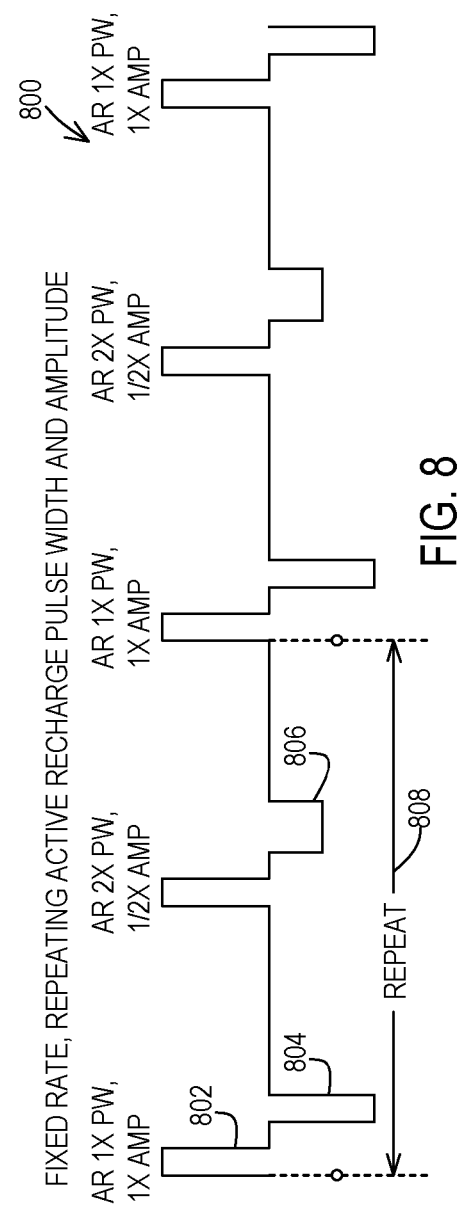

METHODS AND DEVICES THAT UTILIZE HARDWARE TO MOVE BLOCKS OF OPERATING PARAMETER DATA FROM MEMORY TO A REGISTER SET

RELATED APPLICATIONS

The present application claims the benefit of U.S. Provisional Application No. 62/633,063, filed on Feb. 20, 2018.

TECHNICAL FIELD

Embodiments relate to methods and devices that utilize register sets to implement operating parameters. More particularly, embodiments relate to methods and devices that utilize hardware to move blocks of operating parameter data from a memory device to a set of registers.

BACKGROUND

Active devices such as active implantable medical devices that generate electrical stimulation signals utilize a set of registers to hold operating parameter data that is implemented by a given component of the device. For instance, an implantable medical device may include a stimulation engine that creates stimulation waveforms based on waveform parameters that are stored in registers of the stimulation engine. As another example, the implantable medical device may include measurement circuitry to measure operational data such as impedance of a stimulation pathway or voltage of an on-board battery.

In order to control the operation of the component, such as a stimulation engine or measurement circuitry, in many cases the parameter data present in the registers is changed according to a prescribed sequence. For example, for a stimulation engine, the pattern of stimulation pulses may be changed in order to ramp up stimulation amplitudes and then ramp them back down. Other examples include changing the rate and/or pulse width of stimulation pulses, controlling active recharge pulses, and so on.

An active device often utilizes firmware to implement device programming. Firmware programming is implemented by one or more hardware components such as a microprocessor. The term firmware may be used herein without further reference to any underlying hardware for ease of discussion. Therefore, it is to be understood that discussion of actions taken by firmware herein are referring to the actions taken by the hardware implementing the firmware. Firmware is conventionally responsible for changing the operating parameters in the set of registers in order to control the component of interest such as the stimulation engine. However, for circumstances such as controlling the generation of waveforms, the firmware must synchronize the effort to change the parameter values with the operation of the component being controlled so that the changes are able to be implanted by the component at the appropriate time. For instance, in the case of a medical device that provides stimulation therapy, the firmware operations may be on a separate clock from and be asynchronous to the stimulation therapy. The firmware therefore must synchronize to the stimulation being provided for each change of data needed by the stimulation engine in order for the firmware to provide the data necessary to produce the next stimulation waveform amplitude. This creates a significant amount of overhead for the firmware that may overburden the firmware and prevent the firmware from performing other desired functions.

SUMMARY

Embodiments address issues such as these and others by providing a block moving hardware based controller that moves a block of operating parameter data from memory to a set of registers. The block moving hardware based controller receives one or more triggers that causes one or more blocks of the operating parameters to be moved. Multiple individual block mover components of the controller may move respective blocks, each responsive to a dedicated trigger or to a same trigger. Furthermore, a given block mover or individual block mover component may have multiple selectable triggers. Each block of data in memory may include data that is indicative of the block size to cause the block moving hardware based controller to move the proper block size to the set of registers. The block moving hardware based controller may have one or more memory devices to access, and the firmware may write to one memory while the block moving hardware based controller may read from another.

Embodiments provide a method of controlling parameters of an active device that involves writing a plurality of block navigation data and corresponding parameter data and address value pairs to locations within a memory device of a block moving hardware-based controller that comprises a first block mover component and a second block mover component, each block navigation datum and corresponding parameter data and address value pairs defining a block. The method further involves receiving a first trigger at the first block mover component and not at the second block mover component. In response to receiving the first trigger, the method involves reading by the first block mover component a first block navigation datum from the memory device for a first block of the memory device and reading a number of parameter data and address value pairs corresponding to the first block navigation datum. Upon reading the number of parameter data and address value pairs, the method involves writing by the first block mover component the parameter data values that have been read from the memory device by the first block mover component to a set of registers corresponding to the address values that have been read from the memory device by the first block mover component. The method further involves receiving a second trigger at the second block mover component and not at the first block mover component. In response to receiving the second trigger, the method involves reading by the second block mover component a second block navigation datum from the memory device for a second block of the memory device and reading a number of parameter data and address value pairs corresponding to the second block navigation datum. Upon reading the number of parameter data and address value pairs corresponding to the second block navigation datum, the method involves writing by the second block mover component the parameter data values that have been read from the memory device by the second block mover component to a set of registers corresponding to the address values that have been read from the memory device by the second block mover component.

Embodiments provide a method of controlling parameters of an active device that involves writing a plurality of block navigation data and corresponding parameter data and address value pairs to locations within a memory device of a block moving hardware-based controller that comprises a first block mover component and a second block mover component, each block navigation datum and corresponding parameter data and address value pairs defining a block. The method further involves receiving a trigger from a trigger source at the first block mover component and at the second block mover component. In response to receiving the trigger, the method involves reading by the first block mover component a first block navigation datum from the memory device for a first block of the memory device and reading a number of parameter data and address value pairs corresponding to the first block navigation datum. Upon reading the number of parameter data and address value pairs of the first block of the memory device, the method involves writing by the first block mover component the parameter data values that have been read from the memory device by the first block mover component to a set of registers corresponding to the address values that have been read from the memory device by the first block mover component.

Embodiments provide a method of controlling parameters of an active device that involves writing a plurality of block navigation data and corresponding parameter data and address value pairs to locations within a first memory portion of a block moving hardware-based controller, each block navigation datum and corresponding parameter data and address value pairs defining a block. The method further involves receiving a first trigger at the controller. In response to receiving the first trigger, the method involves reading a first block navigation datum from the first memory device for a first block of the first memory portion and reading a number of parameter data and address value pairs corresponding to the first block navigation datum. Upon reading the number of parameter data and address value pairs, the method involves writing the parameter data values that have been read from the first memory portion to a set of registers corresponding to the address values. While reading the number of parameter data and address value pairs from the first memory device, the method involves writing a second plurality of block navigation data and corresponding parameter data and address value pairs to locations within a second memory portion of a block moving hardware-based controller. The method further involves receiving a second trigger at the controller. In response to receiving the second trigger, the method involves reading a second block navigation datum from the second memory portion for a second block of the second memory portion and reading a number of parameter data and address value pairs corresponding to the second block navigation datum. Upon reading the number of parameter data and address value pairs, the method involves writing the parameter data values that have been read from the second memory portion to a set of registers corresponding to the address values read from the second memory portion. While reading the number of parameter data and address value pairs from the second memory portion, the method involves writing a third plurality of block navigation data and corresponding parameter data and address value pairs to locations within the first memory portion.

Embodiments provide a method of controlling parameters of an active device that involves writing a plurality of block navigation data and corresponding parameter data and address value pairs to locations within a first memory device of a block moving hardware-based controller, each block navigation datum and corresponding parameter data and address value pairs defining a block. The method further involves receiving a first trigger at the controller. In response to receiving the first trigger, the method involves reading a first block navigation datum from the first memory device for a first block of the memory device and reading a number of parameter data and address value pairs corresponding to the first block navigation datum. Upon reading the number of parameter data and address value pairs, the method involves writing the parameter data values that have been read from the first memory device to a set of registers corresponding to the address values. The method further involves writing a second plurality of block navigation data and corresponding parameter data and address value pairs to locations within a second memory device of a block moving hardware-based controller. The method involves receiving a second trigger at the controller. In response to receiving the second trigger, the method involves reading a second block navigation datum from the second memory device for a second block of the second memory device and reading a number of parameter data and address value pairs corresponding to the second block navigation datum. Upon reading the number of parameter data and address value pairs, the method involves writing the parameter data values that have been read from the second memory device to a set of registers corresponding to the address values read from the second memory device.

Embodiments provide a method of controlling self-measurements within an active device that involves writing a plurality of block navigation data and corresponding parameter data and address value pairs to locations within a memory device of a block moving hardware-based controller, each block navigation datum and corresponding parameter data and address value pairs defining a block. The method further involves receiving a trigger at the controller. In response to receiving the trigger, the method involves reading a block navigation datum from the memory device for a first block of the memory device and reading a number of parameter data and address value pairs corresponding to the block navigation datum. Upon reading the number of parameter data and address value pairs, the method involves writing the parameter data values that have been read from the memory device to a set of registers corresponding to the address values, the set of registers being control registers of an analog to digital converter of a measurement circuit. The method involves receiving a signal to be measured via the measurement circuit and in accordance with the parameter data values in the set of registers, converting the signal to measurement data.

Embodiments provide a method of controlling an active device that involves writing by a firmware a plurality of block navigation data and corresponding parameter data and address value pairs to locations within a memory device of a block moving hardware-based controller, each block navigation datum and corresponding parameter data and address value pairs defining a block. The method further involves outputting a first trigger from a first trigger source to a multiplexer that is coupled to the first trigger source, to a second trigger source, and to the controller. The method further involves outputting a second trigger from the second trigger source to the multiplexer. At the multiplexer, the method involves selecting one of the first trigger and the second trigger. The method further involves receiving the selected trigger at the controller. In response to receiving the selected trigger, the method involves reading a block navigation datum from the memory device for a first block of the memory device and reading a number of parameter data and address value pairs corresponding to the block navigation datum. Upon reading the number of parameter data and address value pairs, the method involves writing the parameter data values that have been read from the memory device to a set of registers corresponding to the address values, the set of registers being control registers of an analog to digital converter of a measurement circuit.

Embodiments provide a method of controlling stimulation waveform generation in an active implantable medical device that involves writing a plurality of block navigation data and corresponding parameter data and address value pairs to locations within a memory device of a block moving hardware-based controller, each block navigation datum and corresponding parameter data and address value pairs defining a block. The method further involves receiving a trigger at the controller. In response to receiving the trigger, the method involves reading a block navigation datum from the memory device for a first block of the memory device and reading a number of parameter data and address value pairs corresponding to the block navigation datum. Upon reading the number of parameter data and address value pairs, the method involves writing the parameter data values that have been read from the memory device to a set of registers corresponding to the address values, the set of registers being control registers of a waveform generator circuit. The method further involves generating a waveform corresponding to the data values in the set of registers. Upon generating the waveform, the method involves re-writing the parameter data values of the waveform to the set of registers to repeat the generating of the waveform when both a control condition occurs and a value in a control register of the block moving hardware-based controller indicates that the waveform should repeat when the control condition occurs by the block moving hardware-based controller re-writing the parameter data values of the waveform to the set of registers. Upon generating the waveform, the method involves stopping the block moving hardware-based controller from further writing to the registers of the set when both the control condition occurs and the value in the control register indicates that the block moving hardware-based controller should terminate when the control condition occurs so that a final pulse of the waveform is repeated until parameter data values of a waveform are written to the register set.

Embodiments provide a method of controlling an active device that involves writing a starting address value to a storage location. The method further involves writing a plurality of block navigation data and corresponding parameter data and address value pairs to locations within a memory device of a block moving hardware-based controller beginning at the starting address, each block navigation datum and corresponding parameter data and address value pairs defining a block. The method further involves receiving a trigger at the controller. In response to receiving the trigger, the method involves reading a block navigation datum from the memory device for a first block of the memory device and reading a number of parameter data and address value pairs corresponding to the block navigation datum by starting at an address of the memory corresponding to the starting address value. Upon reading the number of parameter data and address value pairs, the method involves writing the parameter data values that have been read from the memory device to a set of registers corresponding to the address values.

DESCRIPTION OF THE DRAWINGS

FIG. 6 shows another example of a waveform produced by a component of an active device where there is a fixed rate and amplitude but random pulse width.

FIG. 7 shows another example of a waveform produced by a component of an active device where there is a fixed rate and pulse width but repeating amplitude changes.

FIG. 8 shows another example of a waveform produced by a component of an active device where there is a fixed rate but an active recharge phase with repeating pulse width and amplitude changes.

DETAILED DESCRIPTION

Embodiments provide block moving hardware based controllers that receive a trigger to move a block of data from memory to a set of registers. This dedicated hardware based controller maintains synchronization with operations of components being controlled by the data values in the set of registers while relieving other devices such as firmware from moving the data to the registers. The data of a given block may indicate the block size and the hardware based controller may then read block navigation data indicative of block size and move the block of data accordingly. The block moving hardware based controller may include multiple block mover components, each receiving its own trigger or sharing a trigger with one or more other block mover components. Furthermore, multiple triggers may exist for a given block mover component and the appropriate trigger is selected. Additionally, the block moving hardware based controller may have access to multiple memory portions or devices, allowing for firmware to write to one memory portion or device while the block moving hardware based controller reads from another memory portion or device.

Figure 1:
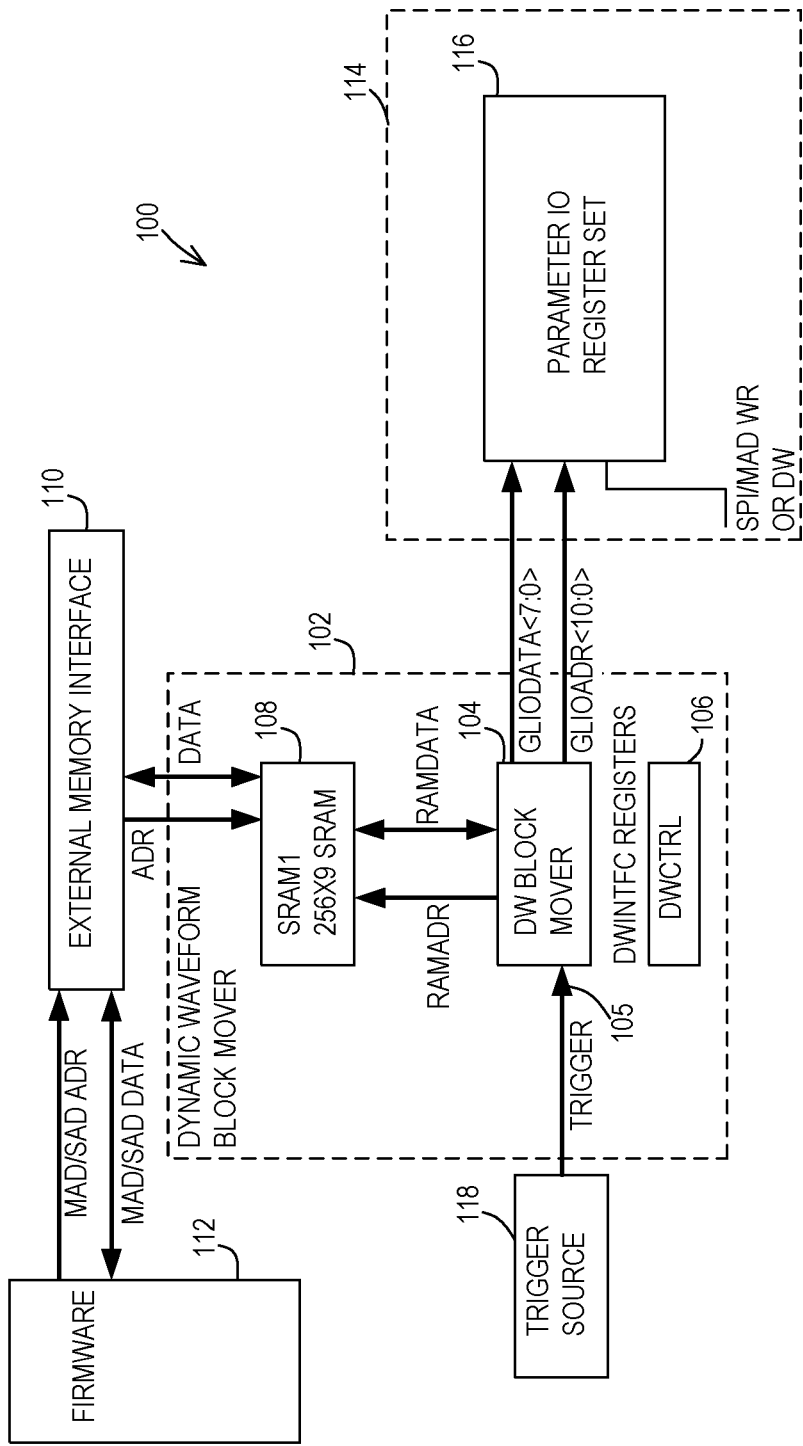
FIG. 1 shows a block diagram of an active device having a block mover.

FIG. 1 shows one example of an active device 100 such as an implantable medical device that includes a block moving hardware based controller 102. The controller 102 includes a block mover hardware component 104 that interfaces with a memory device 108 (e.g., SRAM). The block mover hardware component 104 also includes a trigger input 105 and a set of registers 106 that enable the hardware component 104, selects the particular trigger inputs where there are multiple ones present, and selects the memory segments for multiple triggered inputs. Additionally, the block mover hardware component 104 has an interface to a set of registers 116 of a component 114, such as a stimulation engine or measurement circuit of an implantable medical device. The controller 102 may be constructed of an application specific integrated circuit, hardwired digital logic, stimulus control, and the like.

The memory device 108 has an external memory interface 110 that allows the memory to be accessed by components external to the controller 102. For instance, a firmware component 112, which is one or more hardware components implementing firmware as previously discussed, may write to the memory device 108 via the external memory interface 110 in order to write data to a plurality of memory blocks. Other devices may write to the memory 108 rather than firmware 112, such as an external hardware controller, a programmer, and so forth. In addition to parameter data for controlling the component 114, the data being written to the memory blocks of the memory device 108 may include block navigation data that specifies the block size and interval data that specifies the number of triggers to occur before moving forward with reading and writing the next block of data. The contents of the memory blocks within the memory device 108 are discussed in more detail below with reference to FIG. 3.

A trigger source 118 provides a trigger signal to the trigger input 105 of the block mover hardware component 104. The trigger source may be of various types. For instance, the trigger source may be a timer. As another example, the trigger source 118 may be a trigger output generated by the component 114. For example, the component 114 may be a stimulation engine that behaves as a state machine running in a loop where the completion of each loop results in generation of a trigger signal. As another example, the component 114 may include a stimulation efficacy feedback that acts as a trigger, where in one example a positive efficacy may result in no trigger being generated while a negative efficacy may produce a trigger provided to the block mover hardware component 104.

Figure 2:
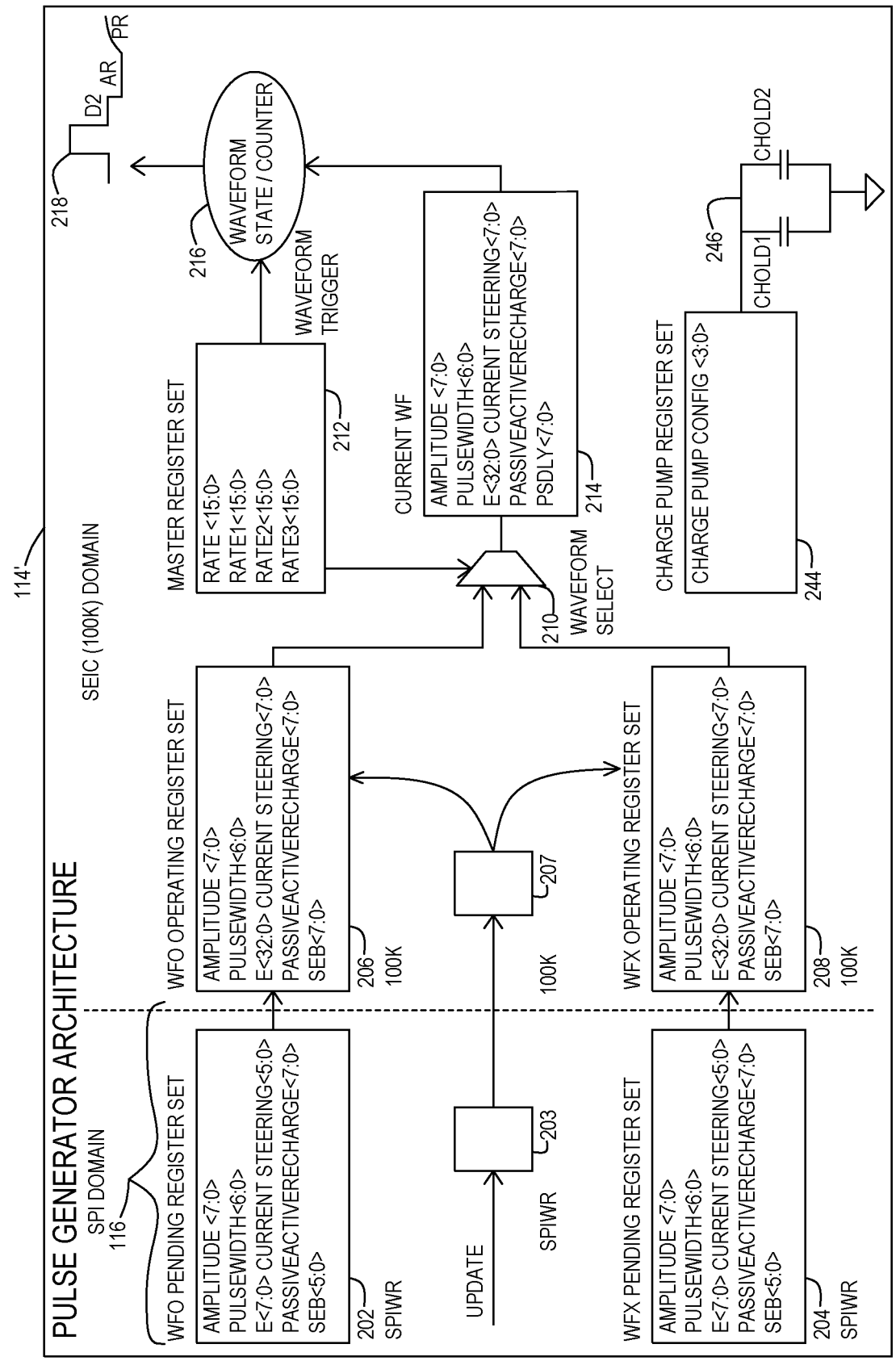
FIG. 2 shows a block diagram of a stimulation engine that is controlled by a set of registers that are programmed to produce a particular waveform according to various embodiments.

FIG. 2 shows an example of such a state machine implementation 114' of the component 114 from FIG. 1. In this example, the component 114' is a waveform generator such as a stimulation engine that produces a one or more electrical pulses per loop. The component 114' includes a first set of waveform parameter registers 202 for a first waveform. Additional sets of pending waveform parameter registers 204 may be included for each additional waveform that may be used during a loop of the state machine. A pending update register 203 may also be included and is discussed further below.

In this example, the component 114' operates one block ahead of the controller 102 by including operating register sets 206, 208 in addition to the pending register sets 202, 204. The operating register sets 206, 208 hold the parameter data that was loaded into the pending register sets 202, 204 in the previous loop. Upon the block moving controller 102 being triggered to move data from the memory 108 to the pending registers 116, a value is also written to the update register 203 by the block moving controller 102 that triggers the component 114' to move the parameter values from the pending register sets 202, 204 to the operating register sets 206, 208 at the next rate interval update trigger. The update register 203, being asserted upon the next rate interval trigger occurring, is represented as update register 207 showing that the update register 207 has resulted in the update of the operating registers 206, 208.

In this example, each output channel of the component 114' has a waveform selector 210 that accesses any one of the operating registers 206, 208 for the particular output channel in order to implement the parameters of a selected waveform to produce the electrical waveform from the output channel. For instance, in an implantable medical device, the waveform selector 210 may choose the particular waveform to be implemented at a given time for a given electrode on an implantable medical lead. The selected waveform is represented in this depiction as a current waveform register 214. The operation of the waveform selector 210 is controlled by a master register set 212. The selected waveform of the current waveform register 214 and the waveform trigger specified by the master register set 212 defines the waveform state and waveform counter of the electrical waveform output 218 of the given output channel. Based on the specified delays between the current pulse and the next pulse, the waveform selector 210 then selects the next waveform register set to cause the next waveform to be output, and so on until the waveform sequence of the sets of registers is complete.

The component 114' of this example that produces an electrical waveform includes a charge pump register set 244. This register set 244 dictates the charging of a bank 246 of hold capacitors that provide the electrical energy to produce each electrical waveform in the series of waveforms. The chare pump operation is not directly related to the block moving controller 102.

Figure 3:
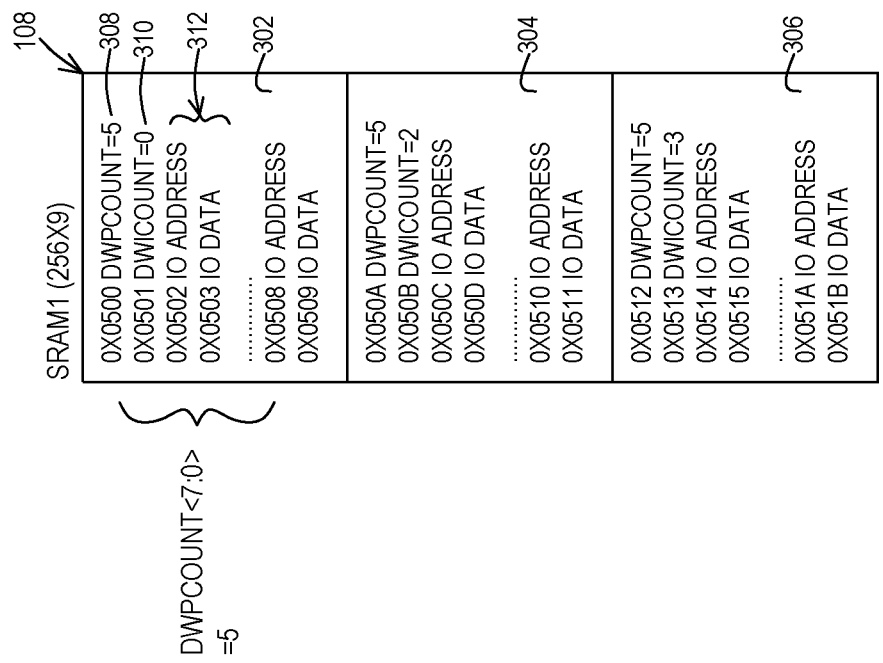
FIG. 3 shows a configuration of memory of an active device according to various embodiments.

FIG. 3 shows an example of how memory blocks are established within the memory device 108 of FIG. 1. Three memory blocks 302, 304, 306 are shown in this example, with each memory block having sequential memory locations. Each memory block may utilize a memory location at a dedicated position within the block, such as the first memory location, that specifies where the next block begins. In this example, each memory block includes a first memory location 308 that provides a block navigation datum to indicate the size of the block by specifying a parameter count that indicates how many pairs of data to read in order to read the entire memory block. In this example, the parameter count is five which indicates that ten memory locations providing five pairings should be read, which includes the pairing that has the count. As another example, the dedicated memory location such as the first memory location 308 may include a block navigation datum that specifies a memory address that indicates where the next block begins. For instance, the memory location may include a block navigation datum that specifies the last address of the current block, such as 0x0509 or specifies the first address of the next block, such as 0x050A, in order to indicate the block size.

Each parameter data pair 312 includes a parameter address value and a parameter data value, where the address value specifies the pending register of register set 116 where the parameter data value should be written. The parameter data value specifies the characteristic of the operation of the component 114, such as a pulse amplitude, pulse width, pulse rate, and so forth where the component 114 generates a waveform. One of the parameter data and address data pairings corresponds to the update data that is moved to the update register 203 as in FIG. 2 to cause the component 114' to move the data in the pending register sets to the operating register sets.

This example also includes a dedicated memory location, such as a second memory location 310, that stores an interval count. In this example, the second memory location is paired with the first memory location 308 that stores the parameter count such that these two memory locations 308, 310 are in a designated location, namely, the first two locations of the block such that the block mover 104 is configured to read these first two memory locations to obtain the parameter and interval counts. The interval count specifies how many triggers should be received by the block mover 104 before reading and writing the next memory block to the pending registers 116. In this example, the memory block 302 specifies that the interval count is zero such that the block mover should not skip any trigger when moving the parameter data of memory block 304. Thus, once the block mover 104 has moved the parameter data of memory block 302 to the pending registers 116, then on the next rate interval block mover trigger, the block mover 104 moves the parameter data of block 304 to the pending registers 116. The memory block 304 specifies an interval count of 2 such that the block mover 104 skips two rater interval block mover triggers before reading the memory block 306 and writing those contents to the pending register set 116.

Figure 4:
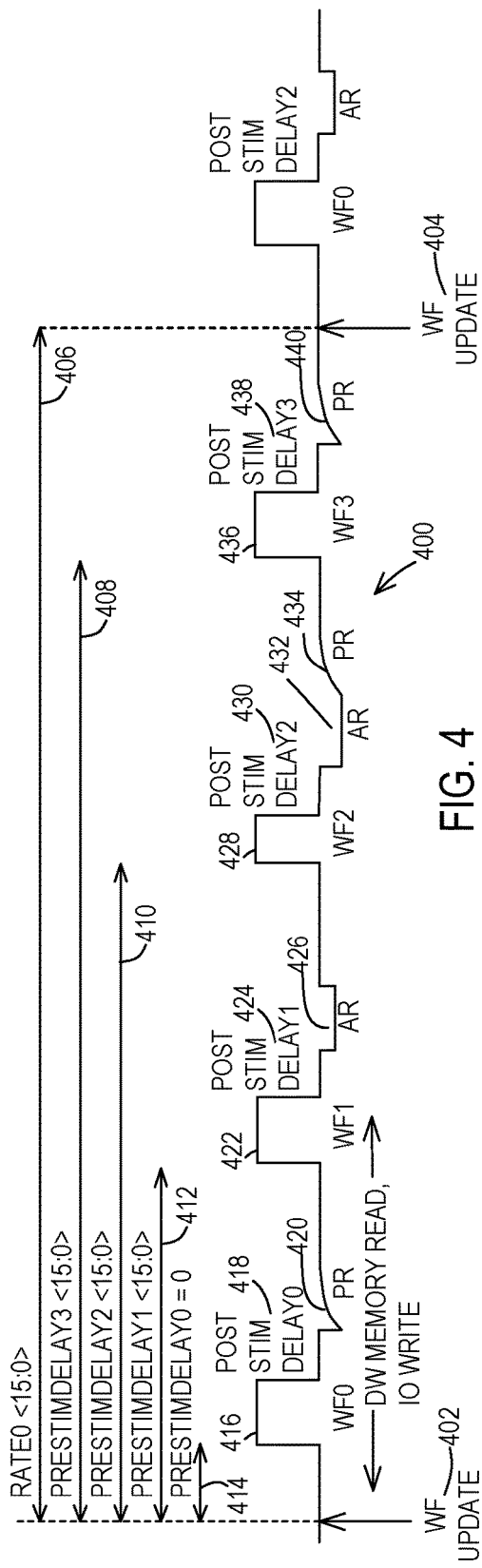
FIG. 4 shows an example of a waveform produced by a component of an active device and shows related parameters that are moved from memory to a set of registers.

FIGS. 4-10 show examples of waveforms formed by a series of individual waveform pulses that may be generated by the active device 100 during a single rate period where parameters of those waveform pulses are specified in the blocks of memory 108 that are ultimately moved by the block mover 104 to the pending register set 116 of the component 114 that produces the waveforms. In FIG. 4, a series of pulses are present for one loop of the waveform state machine through each register set. The timing is such that the operating registers are updated based on the data in the pending registers at a first rate interval update 402, then there are four individual waveform pulses in sequence.

After reaching the end of a first specified delay 414 after the update trigger, the first waveform is produced that has a pulse 416 with a specified amplitude and width, then a specified delay 418, and then a recharge phase 420 which is specified as a passive recharge. Upon completion of a second specified delay 412 after the update trigger, the second waveform is produced that has a pulse 422 with a specified amplitude and width, then a specified delay 424, and then a recharge phase 426 which is specified as an active recharge. Upon completion of a third specified delay 410 after the update trigger, the third waveform is produced that has a pulse 428 with a specified amplitude and width, then a specified delay 430, and then a specified active recharge phase 432 of a given width and then a specified passive recharge phase 434. Upon completion of a fourth specified delay 408 after the update trigger, the fourth and final waveform of this update iteration is produced that has a pulse 436 with a specified amplitude and width, then a specified delay 438, and then a specified passive recharge phase 440.

Upon completion of a rate period 406, an update trigger of a next rate interval is generated that results in a waveform update 404, where pending registers 202, 204 are written to operating registers 206, 208. Parameter data in memory 108 is then written to the pending registers 206, 208 by the block mover 104 during this next rate interval at the appropriate block mover trigger, which may be the same as the trigger of the next rate interval such as WF0 or may be another trigger during the interval.

Relating FIGS. 2, 3, and 4, one example of an implementation may utilize four waveform registers WF0-WF3, each waveform register describing a single pulse plus recharge as shown in FIG. 4. Thus, for a single rate interval 406, each waveform register produces a pulse and recharge for a total of four pulses and recharges. Likewise, the pending register set 116 and operating register set includes the four individual waveform registers. The memory blocks may then specify one or more parameter values per waveform. For instance, each data location and address location pair 312 in memory block 302 may specify a parameter value and register location for each waveform register WF0-WF3. For instance, the block 302 may specify a pulse amplitude for each waveform, where the amplitude may be the same, as shown in FIG. 4, or may ramp upward as discussed in more detail below in relation to FIG. 5.

Any one of the waveforms WF0-WF3 may serve as the trigger source 118 of FIG. 1 for the block moving component 104. Thus, at some point within the rate interval 406, the block mover 104 moves the data from the memory 108 to the pending registers. Then at the end of the rate interval 406, the component 114 updates the operating register set with the data from the pending register set 116 that was moved to the pending register set 116 by the block moving component 104.

Figure 5:
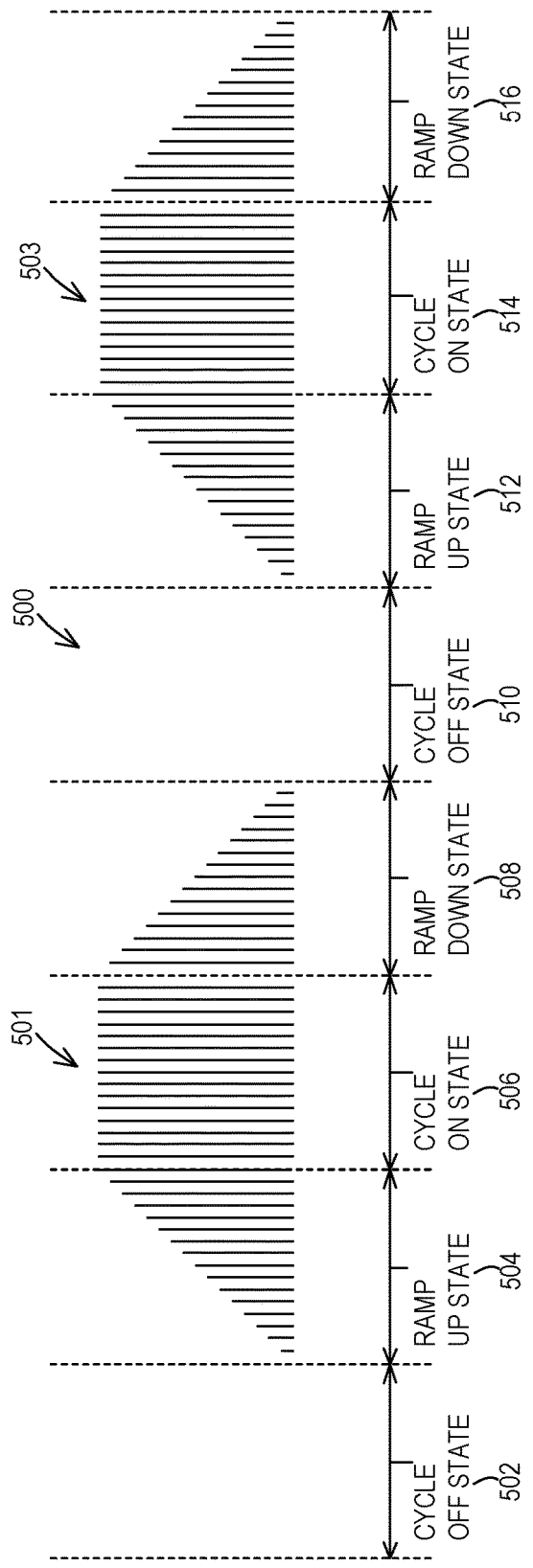
FIG. 5 shows another example of a waveform produced by a component of an active device where the amplitude ramps up and ramps down.

FIG. 5 shows an example 500 where the active device 100 provides a soft start and a soft stop form of stimulation. Here, after a cycle off state 502 ends, the multi-pulse waveform 501 is produced by gradually increasing pulses in specified amplitude during a ramp-up state 504 until reaching a maximum during a cycle on state 506. After completing the maximum amplitude pulses a specified number of times, a parameter can be written to initiate an interrupt, alerting firmware to the completion of the ramp up to the final amplitude. This can be repeated for the ramp down where the waveform 501 begins gradually decreasing the pulse amplitude at a ramp down state 508 until reaching a cycle off state 510. After the specified cycle off state 510, the process may repeat for a subsequent multi-pulse waveform 503 with a ramp up state 512, cycle on state 514, and ramp down state 516. The update trigger may occur after any number of these ramp up/down sequences to alter the multi-pulse waveform.

FIG. 6 shows an example 600 where the active device 100 provides a specified fixed rate and amplitude of pulses but with random pulse widths for a multi-pulse waveform. In this example, there is a specified common pulse amplitude but a specified first pulse width 602, specified second pulse width 604, and specified third pulse width 606. The waveform selector may operate to select the individual waveform pulses from the operating register sets in a random order to produce the random pulse width pulse train as shown.

FIG. 7 shows an example 700 where the active device 100 provides a specified fixed rate and pulse width of pulses but with specified repeating amplitude changes. This example is a ramping down of amplitude, where there are two pulses at a specified maximum amplitude 702, then two pulses of a specified lower amplitude 704, and then two final pulses of the lowest specified amplitude 706. This set of serial waveforms 708 may then repeat for some specified number of triggers. The amplitude changes could instead be a ramping up of amplitude in other examples.

FIG. 8 shows an example 800 where the active device 100 provides a specified fixed rate, amplitude, and pulse width but with a repeating change to an active recharge pulse width and amplitude. For each pulse 802, there is an active recharge pulse of opposite polarity. For the first instance of the pulse 802, there is an active recharge pulse 804 that has an equal but opposite amplitude and an equal pulse width to the pulse 802. For the second instance of the pulse 802, there is an active recharge pulse 806 that has a smaller amplitude but larger pulse width. This set of serial waveforms 808 may then repeat for some specified number of triggers.

Figure 9:
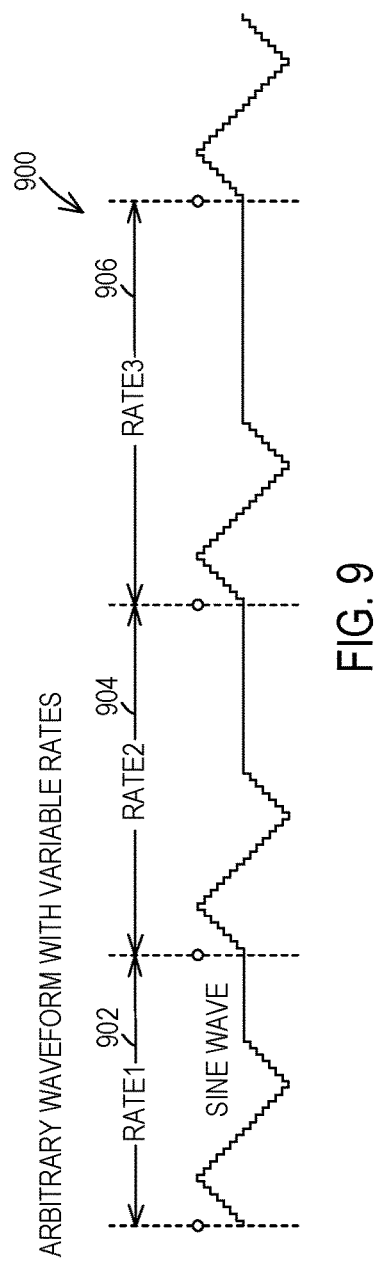
FIG. 9 shows another example of a waveform produced by a component of an active device where there is a varying rate.

FIG. 9 shows an example 900 where the active device 100 provides some waveform shape, in this case a rudimentary sine wave, but with variable rates to each successive waveform. In this example, a first specified waveform rate 902 is the shortest, a second specified waveform rate 904 is longer, and a third specified waveform rate 906 is longest. The waveforms of these three rates 902, 904, 906 may then repeat for some specified number of triggers.

Figure 10:
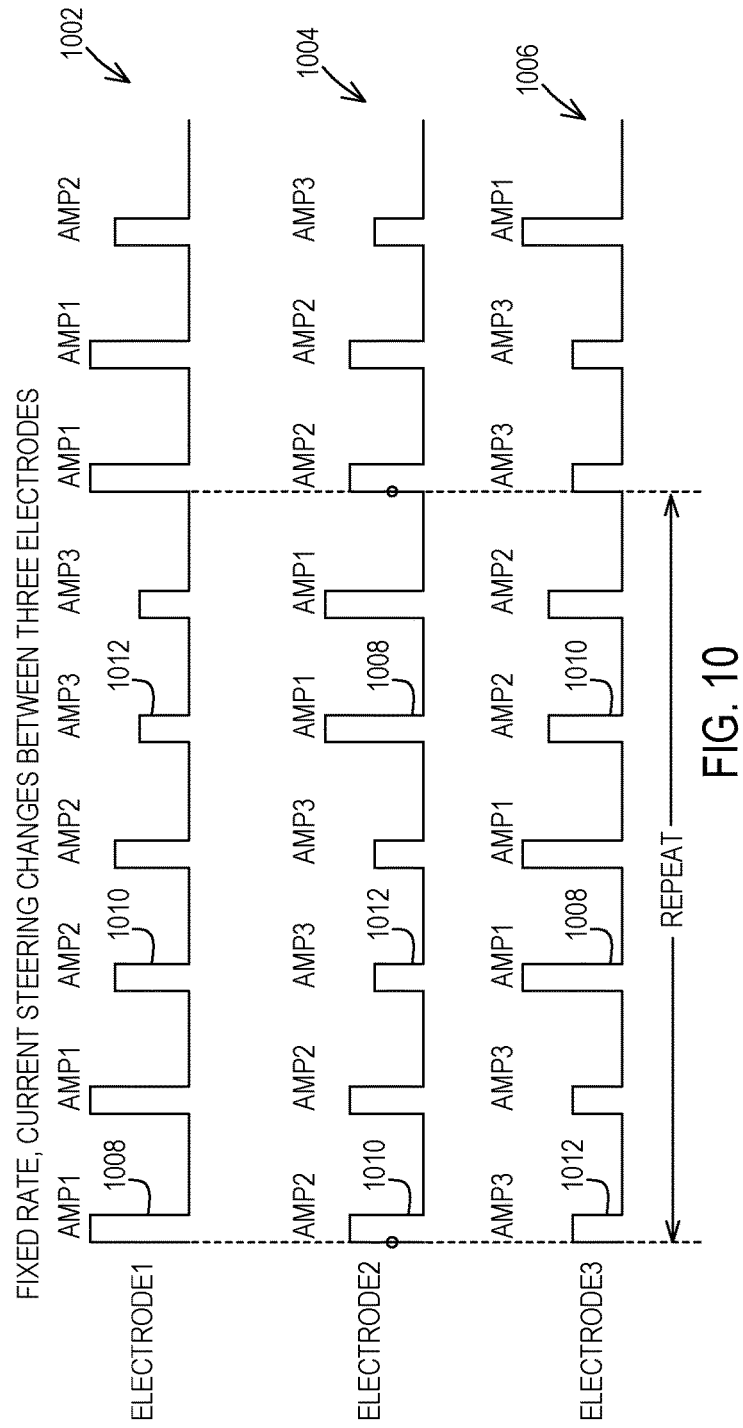
FIG. 10 shows another example of simultaneous waveforms produced by a component of an active device where there is a fixed rate but amplitude differences between the waveforms to give a current steering effect.

FIG. 10 shows an example 1000 of three simultaneous multi-pulse waveforms 1002, 1004, and 1006. Each waveform 1002, 1004, and 1006 is for each of three electrodes of an implantable medical lead of the active device 100, and hence there is one waveform for each corresponding channel of a multi-channel component 114 of the active device 100. These three waveforms 1002, 1004, and 1006 utilize a common pulse width and rate. However, there are three amplitudes 1008, 1010, and 1012 that are present in the three waveforms 1002, 1004, and 1006, and each waveform has a different amplitude than the other two at any given time. This creates a current steering effect for the stimulation therapy being provided by the three corresponding electrodes.

Figure 11:
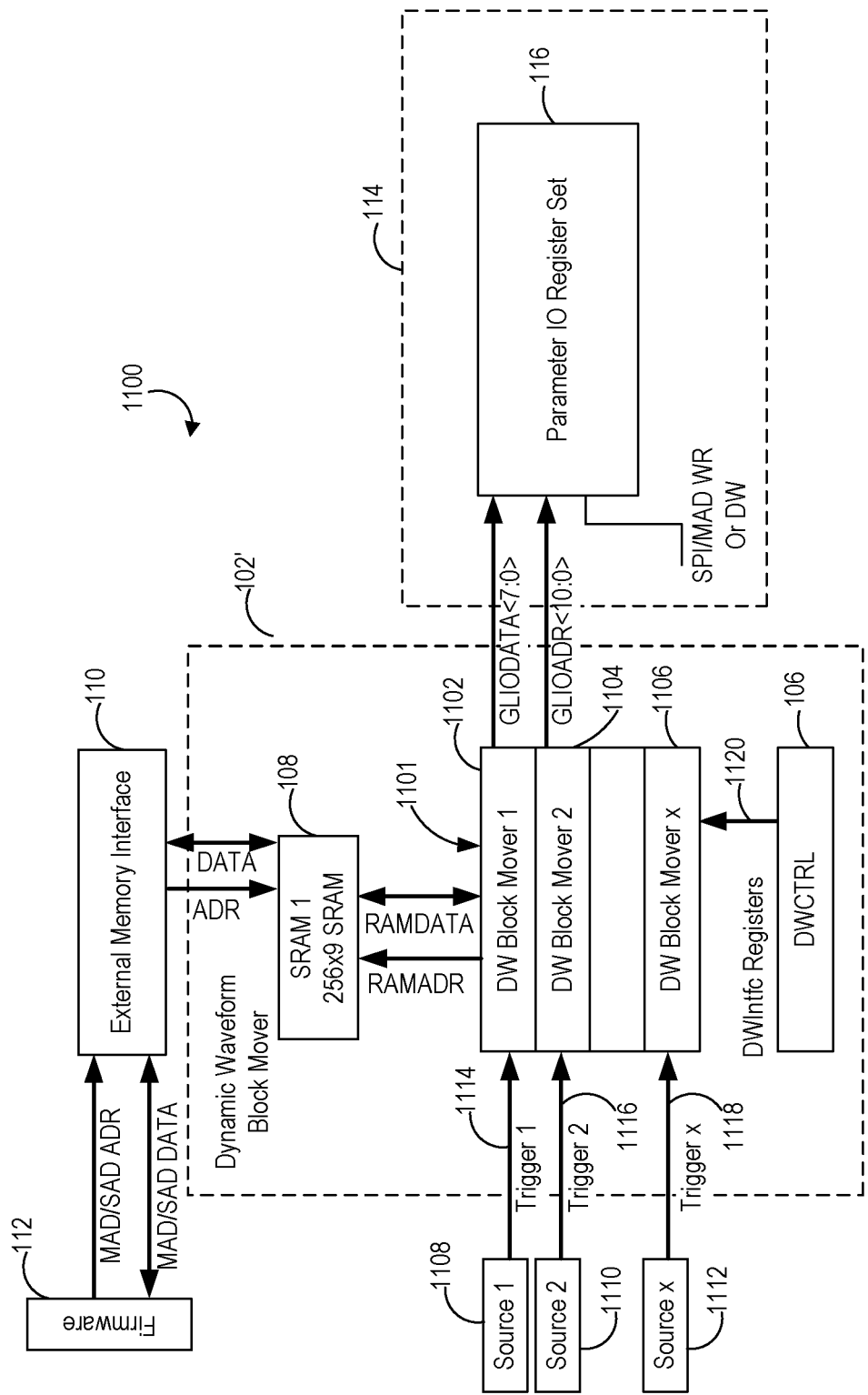
FIG. 11 shows another example of a block diagram of an active device having a block mover but in this example the block mover has several individual block moving devices each with its own trigger source.
Figure 16:
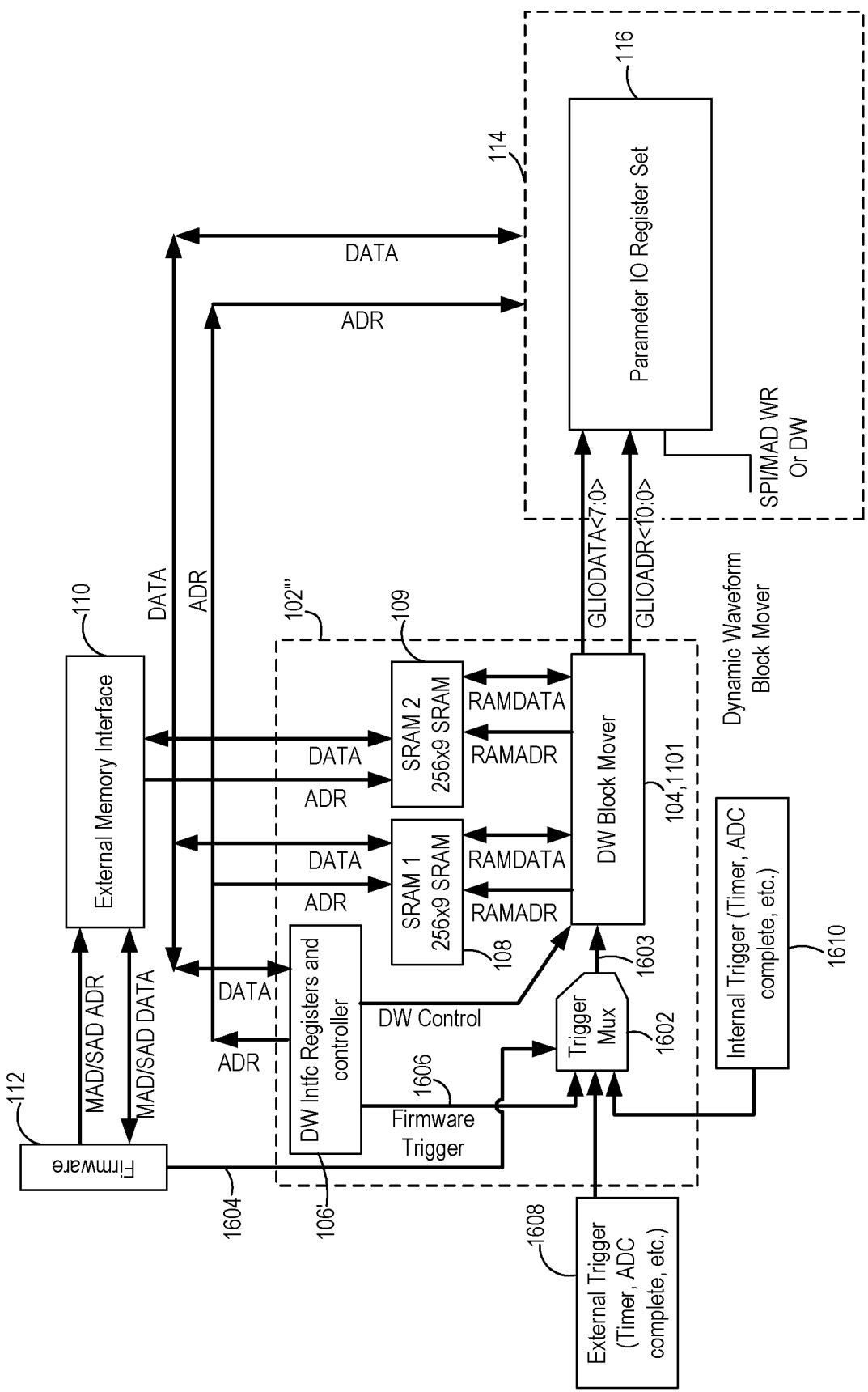
FIG. 16 shows another example of a block diagram of an active device having a block mover and multiple selectable trigger sources.

FIG. 11 shows a different example of an active device 1100 such as an implantable medical device that includes a block moving hardware based controller 102'. The controller 102' includes a set 1100 of multiple block mover hardware components 1102, 1104, 1106 that interface with a memory device 108 (e.g., SRAM). While three block mover hardware components are shown and labeled in FIG. 11, it will be appreciated that any number of hardware components may be included and that three are shown merely as an example. The block mover hardware components 1102, 1104, and 1106 also include dedicated trigger inputs 1114, 116, and 1118, respectively and a set of control registers 106 that enable the hardware components 1102, 1104, and 1106 individually. The control registers 106 may also select the particular memory segments for each block mover component 1102, 1104, 1106 to access as described in more detail below regarding starting address values. Furthermore, the firmware 112 or other external logic may select which trigger source is selected for a given trigger input where there are multiple trigger sources present per trigger input. Examples of this variation are discussed below with reference to FIG. 16.

Additionally, the block mover hardware components 1102, 1104, and 1106 have the interface to the set of registers 116 of the component 114, such as the stimulation engine or measurement circuit of an implantable medical device. As with the example of FIG. 1, the controller 102' of FIG. 11 may be constructed of an application specific integrated circuit, hardwired digital logic, stimulus control, and the like.

The memory device 108 has the external memory interface 110 that allows the memory to be accessed by components external to the controller 102 such as the firmware component 112. The firmware 112 may write to the memory device 108 via the external memory interface 110 in order to write data to a plurality of memory blocks. As with prior examples, other devices may write to the memory 108 rather than firmware 112, such as an external hardware controller, a programmer, and so forth. In addition to parameter data for controlling the component 114, the data being written to the memory blocks of the memory device 108 may include block navigation data that specifies the block size and interval data that specifies the number of triggers to occur before moving forward with reading and writing the next block of data as discussed above in relation to FIG. 3.

In this example, each of the multiple block mover components 1102, 1104, and 1106 has a dedicated trigger source 1108, 1110, 1112, respectively. Each trigger source 1108, 1110, 1112 of this example provides a trigger signal to the trigger input 1114, 1116, 1118, respectively, of the block mover hardware components 1102, 1104, 1106. Each of the trigger sources 1108, 1110, 1112 may be of various types. For instance, the trigger sources may be timers. As another example, the trigger sources may be trigger outputs generated by the component 114, such as a stimulation related trigger or stimulation efficacy related trigger. Considering each trigger input 1114, 1116, 1118 has a dedicated trigger source 1108, 1110, 1112, respectively, when trigger source 1108 provides a trigger to the component 1102, components 1104 and 1106 do not receive the trigger from trigger source 1108. Likewise, when trigger source 1110 provides a trigger to the component 1104, components 1102 and 1106 do not receive the trigger from trigger source 1110, and so on.

The multiple block mover components 1102, 1104, 1106 may be configured in such a way that each is responsible for loading a particular waveform pattern. For instance, there may be four block mover components and four waveform patterns that operate in a sequence with each block mover of the four being responsible for loading a block of memory corresponding to each of the four waveform patterns. In such a case, the trigger source of one block mover component may be triggered upon the completion of a block move by another of the block mover components and/or by the completion of a particular waveform pattern by the stimulation engine or other device. In other situations, each block mover component 1102, 1104, 1106 may be triggered by the independent sources but be triggered simultaneously for parallel operation to move multiple blocks from the memory 108 to the register set 116.

In order to have each block mover component 1102, 1104, 1106 move a particular block of data, each block mover component 1102, 1104, 1106 needs a starting address value corresponding to a starting address in memory for each block mover component. This allows each block mover component to proceed to the starting address corresponding to the assigned starting address value to read the corresponding block of memory including the block navigation datum and the parameter and address value pairs as described above in relation to FIG. 3. In the example shown above in FIG. 3, there are three contiguous blocks 302, 304, and 306 shown and the starting address for a first block 302 of memory is memory address 0x0500, 0x050A for a second block, and 0x0512 for a third block. Thus, one of the block mover components is instructed to begin at this memory address 0x0500 to begin moving the parameter data to the corresponding register address for that particular block of data according to the DWPCOUNT, DWICOUNT values. In this manner, a given block mover component sequences from one block to the next of these contiguous blocks.

However, where there are multiple block mover components 1102, 1104, 1106, as in FIG. 11, each block mover component may be assigned a given set of contiguous blocks, so in this example, the first block mover component 1102 may be assigned starting address 0x0500, while the second block mover component 1104 may be assigned a starting address of a memory block that is not within the contiguous set of blocks assigned to the first block mover component 1102. For instance, if the first block mover component 1102 is assigned only the three contiguous blocks of FIG. 3, then the second block mover component 1104 may be assigned a contiguous set of blocks that begin immediately after the contiguous blocks of FIG. 3 such that the second block mover component 1104 is assigned a starting address of 0x051C. These starting address values may be written by the firmware 112 to a storage location accessible by the block mover components, such as the control registers 106 which then provides a control 1120 to the block mover components to dictate the starting address of each. Other examples of storage locations for the starting address values include dedicated memory locations that the block mover components may be hard coded to access for purposes of obtaining the starting address values.

Figure 12:
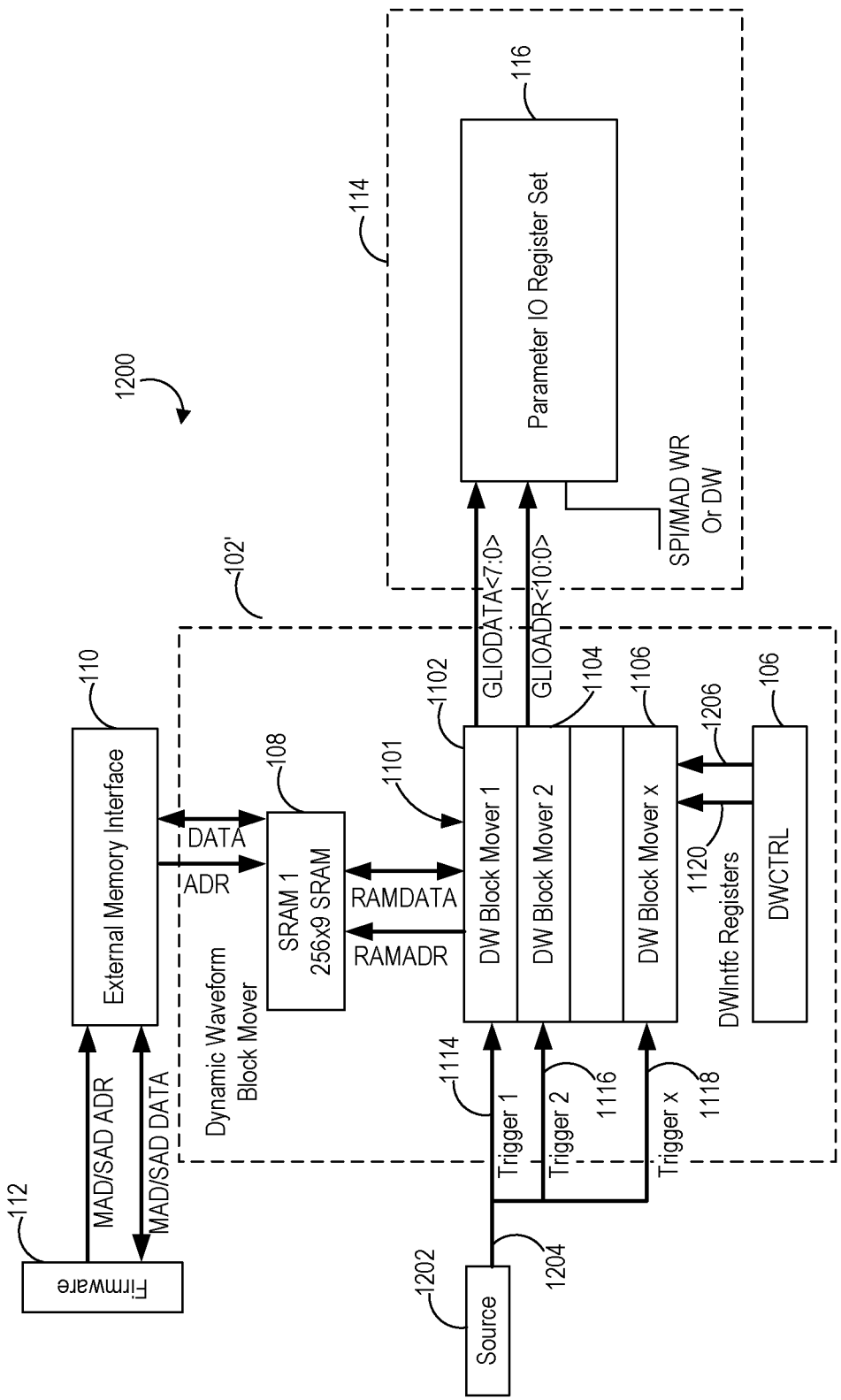
FIG. 12 shows another example of a block diagram of an active device having a block mover but in this example the block mover has several individual block moving devices that share a single trigger source.

FIG. 12 shows a different example of an active device 1200 such as an implantable medical device that includes the block moving hardware based controller 102'. In this example, the controller 102' includes the set 1101 of multiple block mover hardware components 1102, 1104, 1106 like the example of FIG. 11 where each interfaces with the memory device 108 (e.g., SRAM). The block mover hardware components 1102, 1104, and 1106 also include trigger inputs 1114, 116, and 1118, respectively and the set of control registers 106 that enable the hardware components 1102, 1104, and 1106 individually. As with the example of FIG. 11, the control registers 106 may also select the particular trigger inputs where there are multiple ones present, and select the memory segments for multiple triggered inputs. Examples of these variations are discussed below with reference to additional figures.

Additionally, the block mover hardware components 1102, 1104, and 1106 have the interface to the set of registers 116 of the component 114, such as the stimulation engine or measurement circuit of an implantable medical device. Likewise, the memory device 108 has the external memory interface 110 that allows the memory to be accessed by components external to the controller 102 such as the firmware component 112. The firmware 112 may write to the memory device 108 via the external memory interface 110 in order to write data to a plurality of memory blocks. As with prior examples, other devices may write to the memory 108 rather than firmware 112, such as an external hardware controller, a programmer, and so forth. In addition to parameter data for controlling the component 114, the data being written to the memory blocks of the memory device 108 may include block navigation data that specifies the block size and interval data that specifies the number of triggers to occur before moving forward with reading and writing the next block of data as discussed above in relation to FIG. 3.

In this example of FIG. 12, each of the multiple block mover components 1102, 1104, and 1106 share a trigger source 1202. The trigger source 1202 of this example provides a trigger signal to the trigger inputs 1114, 1116, 1118, respectively, of the block mover hardware components 1102, 1104, 1106. The trigger source 1202 may be of various types such as a timer or an output generated by the component 114 such as a stimulation related or stimulation efficacy related trigger.

The multiple block mover components 1102, 1104, 1106 of this example may also be configured in such a way that each is responsible for loading a particular waveform pattern. In such a case, the shared trigger source 1202 of one block mover component may be triggered upon the completion of a block move by another of the block mover components and/or by the completion of a particular waveform pattern by the stimulation engine or other device.

To prevent all block mover components 1102, 1104, 1106 from being simultaneously triggered when that is not desired, the control registers 106 are configured to disable one or more block mover components while enabling one or more block mover components, via control 1206, for a given trigger prior to that trigger occurring. Multiple block movers may be configured to operate in parallel from the shared trigger by the registers 106 being configured so that the control 1206 enables those block mover components that should operate in parallel to move the corresponding memory block. As in FIG. 11, there is also a control 1120 via the control registers 106 to dictate the starting address for each block mover component 1102, 1104, 1106 so that each block mover component begins the block moving procedure at the corresponding assigned starting address in the memory 108.

Figure 13:
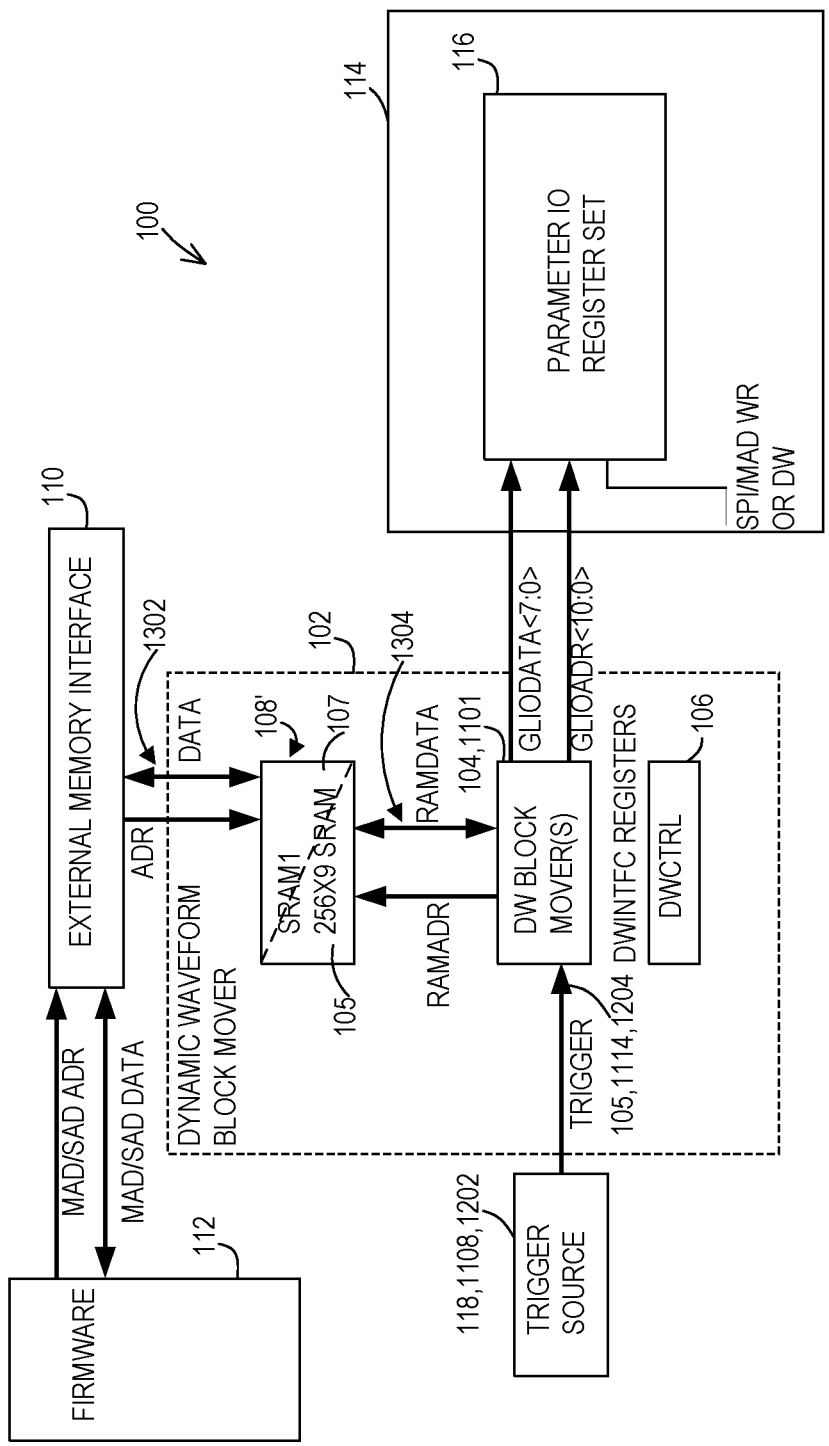
FIG. 13 shows another example of a block diagram of an active device having a block mover but in this example the block mover relies upon a single memory device that is configured to allow the firmware to access one portion of the memory while the block mover accesses as second portion.
Figure 14:
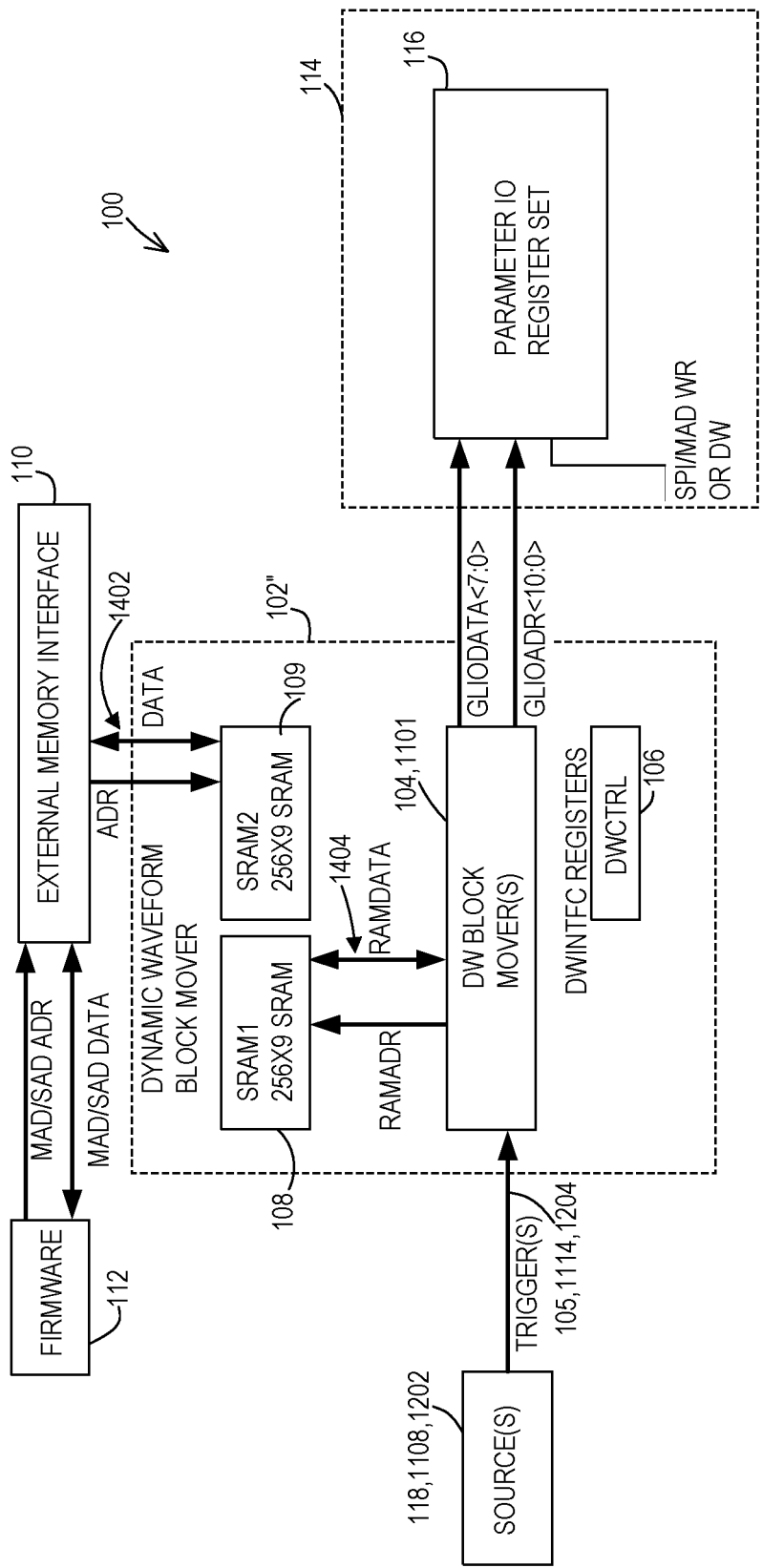
FIG. 14 shows another example of a block diagram of an active device having a block mover but in this example the block mover relies upon two distinct memory devices to allow the firmware to access one memory device while the block mover accesses the second memory device.

FIGS. 13 and 14 illustrate examples where the firmware 112 and the block moving hardware 102 (as in FIG. 13), 102' (as in FIGS. 11 and 12), and 102" (as in FIG. 14), with single or multiple block mover component(s), have access to multiple memory portions (as in FIG. 13) or even separate memory devices (as in FIG. 14). In FIG. 13, a single memory device 108' may be used, such as a multi-port memory, to allow simultaneous access by both the firmware 112 and the block mover device 104, 1101. For purposes of illustration, the memory device 108' is shown as having a first portion 105 and a second portion 107 which corresponds to the ability of access via dual ports. At the instant shown in FIG. 13, the block moving hardware 104, 1101 is accessing the first portion 105 at an access operation 1304 in order to move one or more memory blocks to the set of registers 116 while the firmware 112 is writing memory block data in the second portion 107 at an access operation 1302.

In the example of FIG. 14, there is the first memory device 108 and a second memory device 109 included for the block moving hardware controller 102". Using two distinct memory devices allows each memory device 108, 109 to be a single port memory while still allowing simultaneous access by the firmware 112 and the block mover component(s) 104, 1101. At the instant shown in FIG. 14, the block moving hardware 104, 1101 is accessing the memory device 108 at an access operation 1404 in order to move one or more memory blocks to the set of registers 116 while the firmware 112 is writing memory block data in the separate memory device 109 at an access operation 1402.

Figure 15:
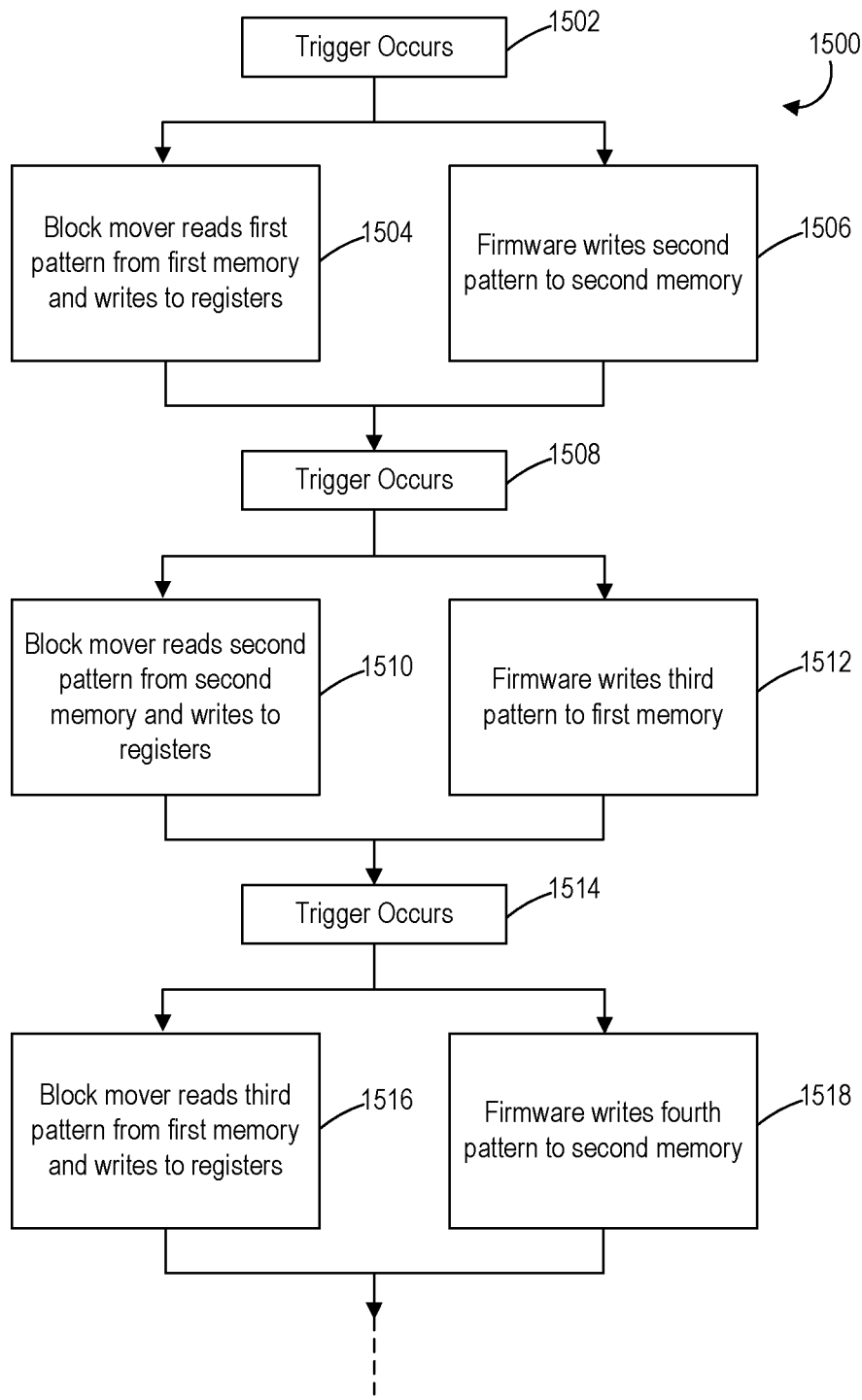
FIG. 15 shows an operational flow of the active device of FIGS. 14 and 15 to allow the firmware to access memory while the block mover also accesses memory.

FIG. 15 shows an example of logical operations 1500 that may be performed by the firmware 112 and the hardware controller 102, 102', or 102" to simultaneously access the memory. This example begins by a trigger occurring at an operation 1502. The trigger causes the block mover hardware to read the first block of data, such as a waveform pattern, from a first memory, such as the memory portion 105 or the memory device 108 at an operation 1504. In parallel, the firmware 112 which either generated the trigger at operation 1502 or monitored the trigger input of the block mover hardware controller 102, 102', 102" then writes a block of data, such as a second pattern, to a second memory portion 107, in the case of a dual port memory, or the memory device 109 in the case of separate memory devices, at an operation 1506. Thus, there has been a simultaneous read and write involving the memory of the block mover hardware controller 102, 102', 102".

A next block move cycle begins by another trigger occurring at an operation 1508. This trigger causes the block mover hardware to read the second block of data, such as a second waveform pattern, from the second memory, such as the memory portion 107 or the memory device 109 at an operation 1510. In parallel, the firmware 112 which either generated the trigger at operation 1508 or monitored the trigger input of the block mover hardware controller 102, 102', 102" then writes another block of data, such as a third pattern, to the first memory, such as the memory portion 105 or the memory device 108 at an operation 1512. Thus, there has been another simultaneous read and write involving the memory of the block mover hardware controller 102, 102', 102".

A third block move cycle begins by another trigger occurring at an operation 1514. This trigger causes the block mover hardware to read the third block of data, such as a third waveform pattern, from the first memory at an operation 1516. In parallel, the firmware 112 which either generated the trigger at operation 1514 or monitored the trigger input of the block mover hardware controller 102, 102', 102" then writes another block of data, such as a fourth pattern, to the second memory at an operation 1518. Thus, there has been a third simultaneous read and write involving the memory of the block mover hardware controller 102, 102', 102". The process of switching back and forth between the memories for reading and writing purposes as shown in FIG. 15 can continue until no additional writing and/or reading is required.

In some cases, it may be desirable for the trigger input(s) of the block mover component(s) described above in relation to FIGS. 1, 11, and 12 to have multiple selectable trigger sources. An example of this is shown for a block mover hardware controller 102''' in FIG. 16. A given block mover component 104, 1101 has a trigger input 1603 that may receive a trigger from one of three trigger sources including a controller/register set 106' that asserts a trigger 1606, an external trigger source 1608 such as an external timer or external analog to digital converter, or an internal trigger source 1610 such as an internal timer or internal analog to digital converter (discussed in more detail below with reference to FIG. 17). In order to provide a trigger from any one of these three trigger sources, a multiplexer 1602 is included. The multiplexer 1602 is connected to each of the three trigger sources and to the trigger input 1603. The multiplexer 1602 has a control 1604 generated by the firmware 112 to allow the firmware to select whichever trigger source is desired at a given time for the block mover component 104, 1101.

It will be appreciated that there may be a separate multiplexer 1602 for each block mover component that will receive an independent trigger. Should multiple block mover components share a trigger, as in FIG. 12, then a single multiplexer 1602 may be present. Additionally, FIG. 16 also further illustrates how these multiple aspects discussed in the previous figures may be combined, as multiple memory devices 108, 109 are included in this example. A single dual port memory may instead be included, or if simultaneous read and write operations of FIG. 15 are not needed, then one single port memory device may be used.

Figure 17:
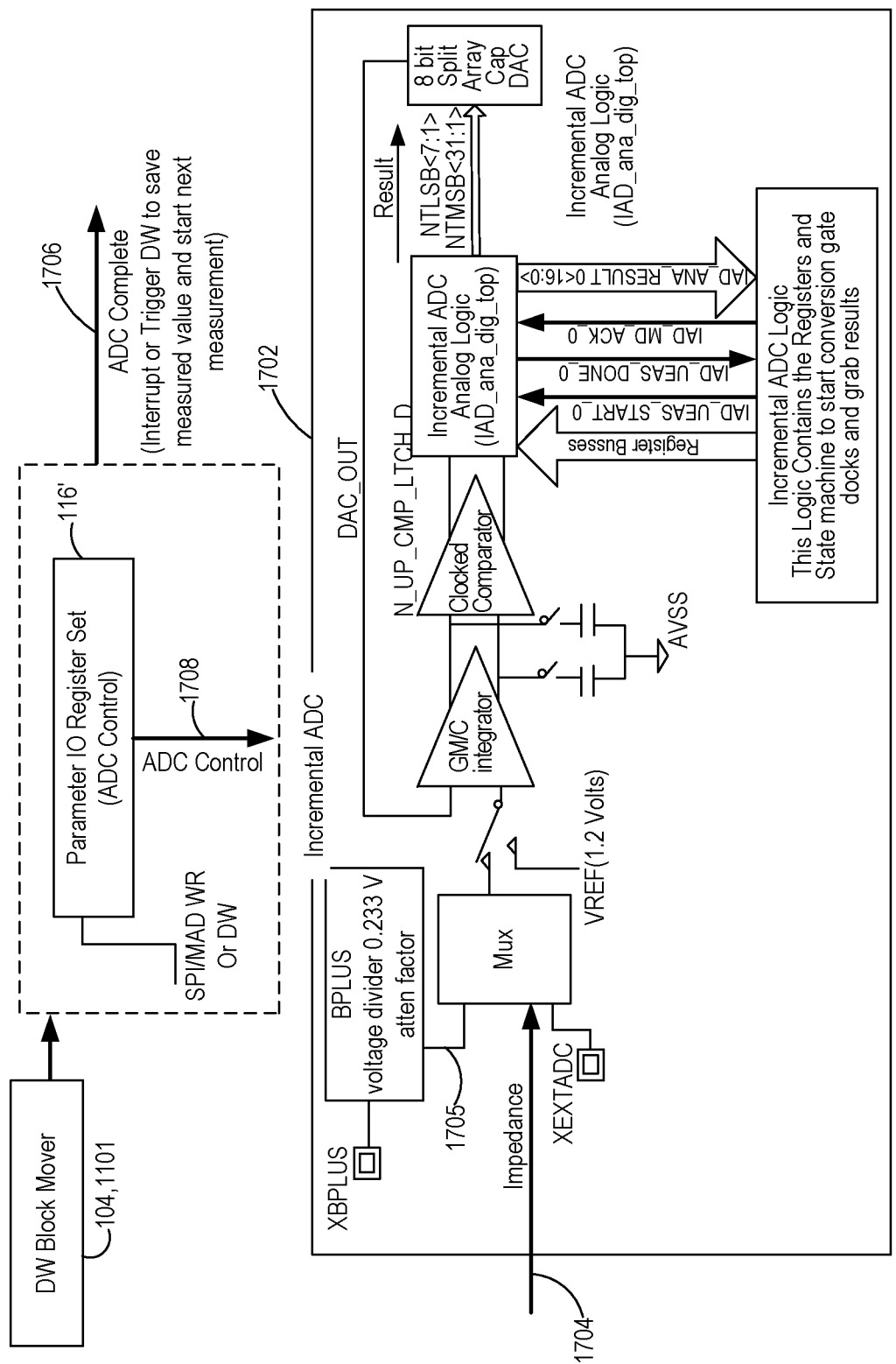
FIG. 17 shows an example of a block mover providing control parameters to a measurement circuit.

FIG. 17 shows another example of using a block mover hardware controller for a particular purpose that involves triggering the block mover hardware controller. In this specific example, the implantable medical device is making self-measurement of operational values. As opposed to a pulse generator as in FIG. 2, the example of FIG. 17 shows that the set of registers 116' corresponds to a measurement circuit 1702. In this specific example, the measurement circuit 1702 is in the form of an incremental analog-to-digital converter (ADC) where the measurement circuit 1702 obtains samples of an analog signal to be measured and converts the analog values to digital values that can then be saved to memory as measurement data for further consideration by the implantable medical device or other host device.

The block mover hardware component 104, 1101 moves a block of memory in the manner that has been described above for the various embodiments, to the register set 116' of the measurement circuit 1702. The data of the block of memory being moved to the register set 116' contains the operational parameters for making the measurement of interest which are illustrated as the control 1708. The measurement circuit 1702 has a signal input that receives the analog signal of interest. In this example, the measurement circuit 1702 may be measuring such operational parameters of an implantable medical device as an impedance of a stimulation pathway, a voltage of an on-board battery, or other external signal.

In this example of FIG. 17, the measurement circuit 1702 is configured to measure multiple values, such as on-board battery voltage and impedance. The input signals such as an impedance input 1704 and a battery voltage input 1705 are then selected by a multiplexer. Conventional methods may be used to perform the analog to digital conversion to result in the digital value being produced. For impedance in particular, the signal 1704 may represent a voltage difference between electrodes which is then converted to impedance by the measurement circuit 1702 based on a known current provided to the electrodes that resulted in the voltage signal 1704. Once the value is ready for saving to memory, the measurement circuit 1702 of this example generates a trigger 1706 which causes a device to write the measurement value to memory. This writing to memory may be performed by the firmware 112 being triggered. Alternatively, when capable of writing to the memory, the hardware based block mover 102, 102', 102", 102''' may write the measurement value to the memory, such as to a dedicated memory location that is defined in the control registers 106.

Figure 18:
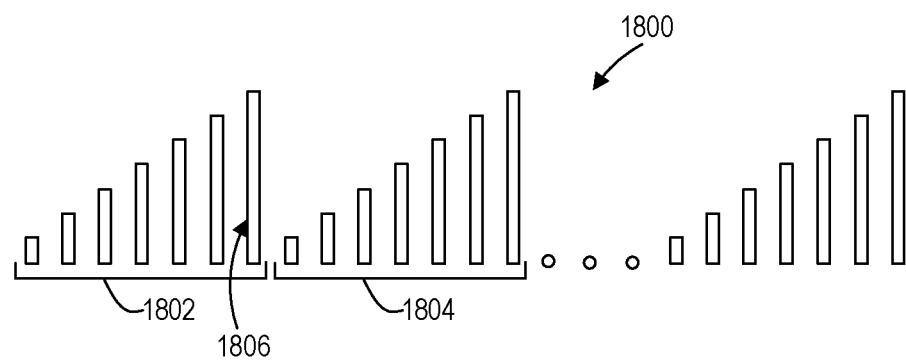
FIG. 18 shows an example of a waveform pattern produced by a waveform generator of an active device where the amplitude repeatedly ramps up by the block mover repeating a block move.
Figure 19:
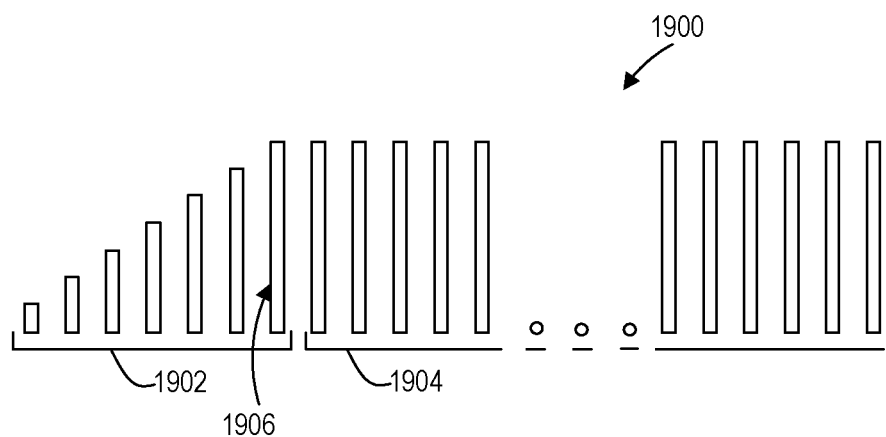
FIG. 19 shows an example of a waveform pattern produced by a waveform generator of an active device where the amplitude ramps up and then repeats the peak value by the block mover terminating once the peak value is reached.

Returning to contexts where the hardware based block mover is being used to move memory blocks that define waveforms, such as stimulation waveforms for an implantable medical device, a control condition may be used to indicate an action to take at the end of a current waveform pattern. FIGS. 18 and 19 show waveform examples that may be of interest. In FIG. 18, the overall waveform pattern 1800 is a series of the same waveform pattern being repeated, as in the first instance 1802 of pulses 1806 forming a waveform pattern and the second instance 1804 of pulses forming the same waveform pattern again. In this particular example, each individual waveform pattern 1802, 1804, is a ramp up pattern. This may be a useful mode of stimulation therapy for certain conditions.

In FIG. 19, the overall waveform pattern 1900 is a waveform pattern 1902 being occurring and then the final pulse 1906 being repeated to form a subsequent waveform 1904. In this particular example, the initial waveform pattern 1902 is a ramp up pattern and the subsequent waveform pattern 1904 is of course a constant magnitude pattern due to the repetition of the final value of the ramp up pattern, which is the pulse with the maximum amplitude. This may also be a useful mode of stimulation therapy for certain conditions.

Figure 20:
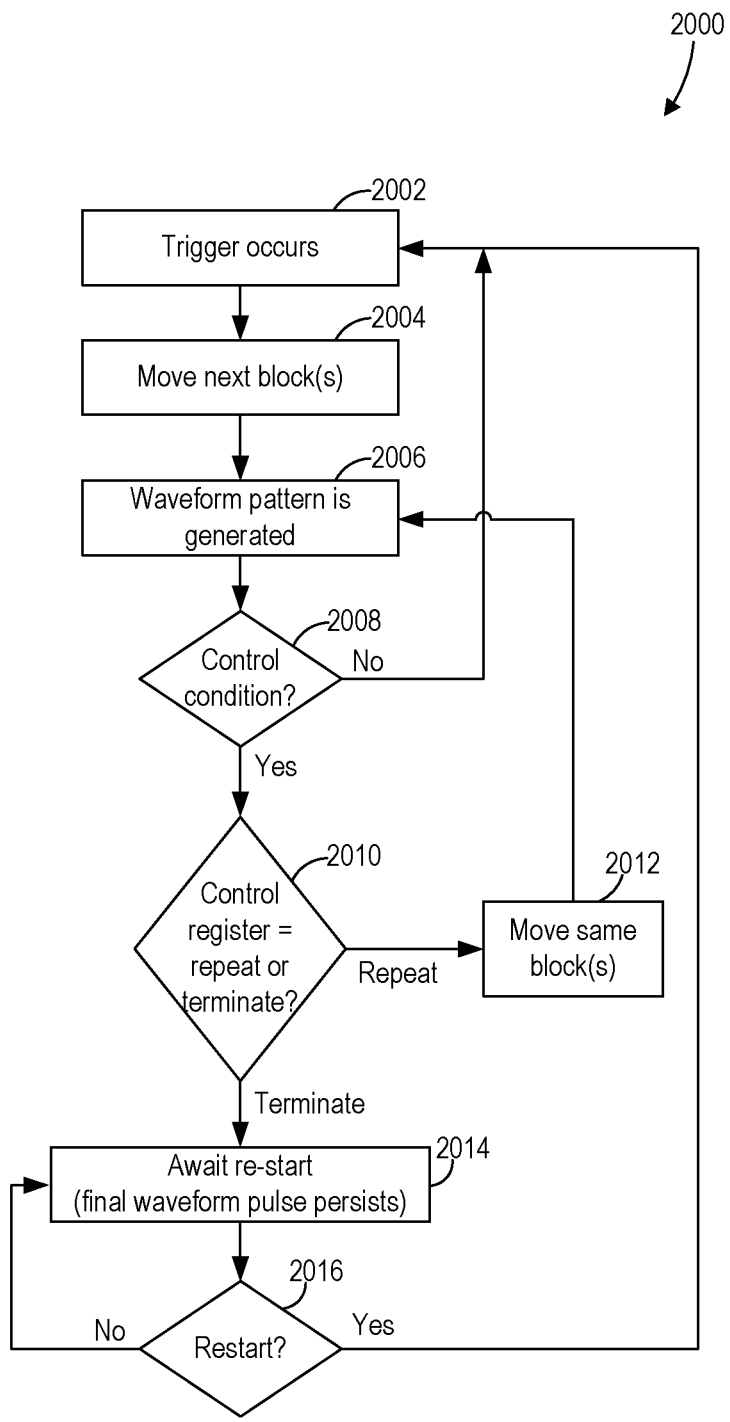
FIG. 20 shows an operational flow of the active device that includes the block mover to produce repetition of a waveform pattern as in FIG. 18 or repetition of a final pulse as in FIG. 19.

One manner of bringing about either of these waveform patterns of FIGS. 18 and 19 is to utilize a control condition and a control register in the register set 106 to dictate the appropriate behavior of the hardware based controller 102, 102', 102", 102'''. FIG. 20 shows an example of logical operations 2000 where the hardware based controller 102, 102', 102", 102''' may operate in such a way that either result can be achieved depending upon whether the control condition is present and depending upon which control register setting has been created by the firmware 112.

Operations of this example begin by the hardware based controller 102, 102', 102", 102''' receiving a trigger at an operation 2002. The hardware based controller 102, 102', 102", 102''' then moves the next block, or multiple blocks in the case of a controller configuration using multiple block mover components, to the register set 116 at an operation 2004. From this block move, the waveform generator like that of FIG. 2 generates a waveform pattern, such as the waveform pattern 1802 or 1902 at an operation 2006.

At this point, the hardware based controller 102, 102', 102", 102''' is responsive to whatever configuration has been created by the firmware 112 or other manner of pre-setting the control registers 116. Specifically, the hardware based controller 102, 102', 102" 102''' determines whether a control condition has occurred at an operation 2008, where the control condition may be hardcoded or specified in the control registers 106. For instance, the hardware based controller 102, 102', 102", 102''' can be configured to determine if a DWICOUNT value is zero for the current memory block as specified a memory location such as location 310 of FIG. 3. As another example, the hardware based controller 102, 102', 102", 102''' can find a termination code as a data value within a certain data location of the current memory block, such as the last memory location. One manner of specifying a termination code is to specify a data value that is considered out of range, such as a value in excess of decimal value 255.

Where no control condition has occurred for the current memory block, then the hardware based controller 102, 102', 102", 102''' awaits the next trigger at operation 2002 in preparation for moving a next block to the register set 116. However, if a control condition is found at operation 2008, then the hardware based controller 102, 102', 102", 102''' takes an action such as that resulting in the waveform pattern of FIG. 18 or FIG. 19. Which action to take could be hardcoded to provide the waveform pattern of FIG. 18 or alternatively hard coded to provide the waveform pattern of FIG. 19. However, the action to take may be specified by the control registers 106 or written to another storage location such as a dedicated memory address so that the firmware 112 can change the setting as desired.

Where specified by the control registers 106 or otherwise, then the hardware based controller 102, 102', 102", 102''' acts accordingly. Thus, if the action to take is specified as a repetition action, then the hardware based controller 102, 102', 102", 102''' proceeds to move the same memory block(s) again at an operation 2012 to thereby re-write the same operational parameters back to the set of registers to cause the waveform generator to repeat the most recent waveform pattern. Thus, this may produce a waveform pattern that repeats like the ramp up waveform pattern of FIG. 18, and the process repeats itself until the firmware 112 changes the control setting to terminate at operation 2010 or ignore the control condition at operation 2008.

If the action to take place is instead specified as a termination action at operation 2010, then the hardware based controller 102, 102', 102", 102''' terminates further action and awaits a re-start of operations by the firmware 112 at an operation 2014, with the determination of whether a re-start has been initiated at an operation 2016. As a result of the hardware based controller 102, 102', 102", 102''' terminating further block moves, the final pulse parameter remains in the active register of the waveform generator such that the final pulse is repeated like the one shown in FIG. 19.

From the embodiments above, it can be seen that there are many variations that can be applied to the hardware based controller 102, 102', 102", 102''' for added flexibility and functionality. There may be multiple trigger sources including multiple selectable trigger sources for a given block mover component, multiple block mover components with separate or same triggers and specified starting address values for each block mover component, multiple memory portions as well as simultaneous reading and writing from/to memory, application of control conditions to end of pattern behaviors, and control of waveform generator circuits as well as other circuit types such as measurement circuits.

While embodiments have been particularly shown and described, it will be understood by those skilled in the art that various other changes in the form and details may be made therein without departing from the spirit and scope of the invention.

What is claimed is:

1. A method of controlling stimulation waveform generation in an active implantable medical device, comprising:
    writing a plurality of block navigation data and corresponding parameter data and address value pairs to locations within a memory device of a block moving hardware-based controller, each block navigation datum and corresponding parameter data and address value pairs defining a block;
    receiving a trigger at the controller;
    in response to receiving the trigger, reading a block navigation datum from the memory device for a first block of the memory device and reading a number of parameter data and address value pairs corresponding to the block navigation datum; and
    upon reading the number of parameter data and address value pairs, writing the parameter data values that have been read from the memory device to a set of registers corresponding to the address values, the set of registers being control registers of a waveform generator circuit;
    generating a waveform corresponding to the data values in the set of registers;
    upon generating the waveform, re-writing the parameter data values of the waveform to the set of registers to repeat the generating of the waveform when both a control condition occurs and a value in a control register of the block moving hardware-based controller indicates that the waveform should repeat when the control condition occurs by the block moving hardware-based controller re-writing the parameter data values of the waveform to the set of registers;

upon generating the waveform, stopping the block moving hardware-based controller from further writing to the registers of the set when both the control condition occurs and the value in the control register indicates that the block moving hardware-based controller should terminate when the control condition occurs so that a final pulse of the waveform is repeated until parameter data values of a waveform are written to the register set.

2. The method of claim 1, wherein the control condition is a termination code in the block data.

3. The method of claim 1, wherein a firmware writes the value to the control register.

* * * * *